United States Patent
Lindhofer

(10) Patent No.: US 9,017,676 B2
(45) Date of Patent: Apr. 28, 2015

(54) DESTRUCTION OF TUMOR CELLS BY TRIFUNCTIONAL BISPECIFIC ANTIBODIES WITH LOW TO MEDIUM EXPRESSION LEVELS OF TUMOR-ASSOCIATED TARGET ANTIGENS

(75) Inventor: Horst Lindhofer, Munich (DE)

(73) Assignee: Horst Lindhofer, Munich (DE)

( * ) Notice: Subject to any disclaimer, the term of this patent is extended or adjusted under 35 U.S.C. 154(b) by 1451 days.

(21) Appl. No.: 12/224,010

(22) PCT Filed: Feb. 15, 2007

(86) PCT No.: PCT/EP2007/051483
§ 371 (c)(1),
(2), (4) Date: Mar. 31, 2010

(87) PCT Pub. No.: WO2007/093630
PCT Pub. Date: Aug. 23, 2007

(65) Prior Publication Data
US 2010/0178298 A1 Jul. 15, 2010

(30) Foreign Application Priority Data
Feb. 15, 2006 (EP) .................................... 06003057

(51) Int. Cl.
A61K 39/395 (2006.01)
C07K 16/28 (2006.01)
C07K 16/30 (2006.01)
C07K 16/32 (2006.01)
A61K 39/00 (2006.01)

(52) U.S. Cl.
CPC ....... *C07K 16/2887* (2013.01); *A61K 2039/505* (2013.01); *A61K 2039/55* (2013.01); *C07K 16/2809* (2013.01); *C07K 16/3084* (2013.01); *C07K 16/32* (2013.01); *C07K 2317/24* (2013.01); *C07K 2317/31* (2013.01); *C07K 2317/73* (2013.01)

(58) Field of Classification Search
None
See application file for complete search history.

(56) References Cited

U.S. PATENT DOCUMENTS

| 6,551,592 | B2 * | 4/2003 | Lindhofer et al. ......... 424/136.1 |
| 2002/0009430 | A1 | 1/2002 | Lindhofer et al. |
| 2002/0051780 | A1 | 5/2002 | Lindhofer et al. |
| 2003/0223999 | A1 | 12/2003 | Lindhofer |
| 2005/0255110 | A1 | 11/2005 | Lindhofer et al. |
| 2006/0115481 | A1 | 6/2006 | Lindhofer et al. |

FOREIGN PATENT DOCUMENTS

| AU | 2007216472 | 5/2013 |
| DE | 195 31 346 | 2/1997 |
| DE | 196 49 223 | 3/1998 |
| DE | 198 59 110 | 4/2000 |
| WO | WO 95/33844 | 12/1995 |
| WO | WO 00/18435 | 4/2000 |
| WO | WO 00/18806 | 4/2000 |
| WO | WO 02/20039 | 3/2002 |
| WO | WO2007/093630 | 8/2007 |

OTHER PUBLICATIONS

Granziero, Krajewski, Farness, Yuan, Courtney, Jackson, Peterson, and Vitiello. Adoptive immunotherapy prevents prostate cancer in a transgenic animal model. European Journal of Immunology, 1999. vol. 29 pp. 1127-1138.*
Byers. What can randomized controlled trials tell us about nutrition and cancer prevention? CA Cancer Journal, 1999. vol. 49, pp. 353-361.*
Freshney. Culture of Animal Cells, A Manual of Basic Technique, Alan R. Liss, Inc., 1983, New York, p. 4.*
White et al. (2001, Ann. Rev. Med., 2001, 52:125-145).*
Meibohm (Pharmacokinetics and Pharmacodynamics of Biotech Drugs, Wiley-VHC, 2006, chapter 3, p. 45-91).*
Sen et al (Journal of Hematotherapy & Stem Cell Research, 2001, 10:247-260).*
Ruf et al (2001, Blood, 98:2526-2534).*
Ruf et al (2004, Int J Cancer, 108:725-732).*
Gall et al (Experimental Hematology, 2005, 33:452-459).*
Hainfeld et al (The British Journal of Radiology, 2011, 84:526-533).*
Faltin et al., *Bl20, a Novel Trifunctional Bispecific Antibody (CD20XCD3), Mediates Efficient Killing of B-Cell Lymphoma Cells In Vitro by Activation of T Cells and CD14+-Accessory Cells*. Blood. 44th Annual Meeting of American Society of Hematology; Philadelphia, PA, USA: Dec. 6-10, 2002 [Abstract].
*Final Data from Two Phase II Trials Indicate Activity of Adecatumumab (MT201) in Breast and Prostate Cancer*. Hugin via COMTEX News Network. Carlsbad, CA, and Geneva, Switzerland. Oct. 2, 2006.
Gatzemeier et al., *Randomized phase II trial of gemcitabine-cisplatin with or without trastuzumab in HER2-positive non-small-cell lung cancer*. Annal of Oncology. vol. 15 pp. 19-27 (2004).
Heiss et al., *Immunotherapy of malignant ascites with trifunctional antibodies*. International Journal of Cancer. vol. 117 pp. 435-443 (2005).
Kiewe et al., *Phase I Trial of the Trifunctional Anti-HER2 x Anti-CD3 Antibody Ertumaxomab in Metastatic Breast Cancer*. Clinical Cancer Research. vol. 12, No. 10 pp. 3085-3091 (2006).
Kiewe et al., *Phase I trial of the trifunctional anti-HER2 x anti-CD3 antibody ertumaxomab in metastatic breast cancer*. Journal of Clinical Oncology. 2005 ASCO Annual Meeting Proceedings. vol. 23, No. 16S (Jun. 1 Supplement) (2005) [Abstract].

(Continued)

*Primary Examiner* — Laura B Goddard
(74) *Attorney, Agent, or Firm* — Jenkins, Wilson, Taylor & Hunt, P.A.

(57) ABSTRACT

The use of trifunctional bispecific antibodies for the preparation of a pharmaceutical composition for the prophylaxis and treatment of tumor diseases is provided. Trifunctional bispecific antibodies bind to tumor-associated antigens including Her2/neu, CD20, EpCAM, G250, proteoglycans, GD3, GD2, MHC II, EGF-R and CEA expressed on tumor cells at low to medium expression levels. Also provided are methods for the treatment or prophylaxis of tumor diseases by administering a pharmaceutically effective amount of a trifunctional bispecific antibody to a patient in need thereof.

18 Claims, 20 Drawing Sheets

(56) References Cited

OTHER PUBLICATIONS

Figure 5A:
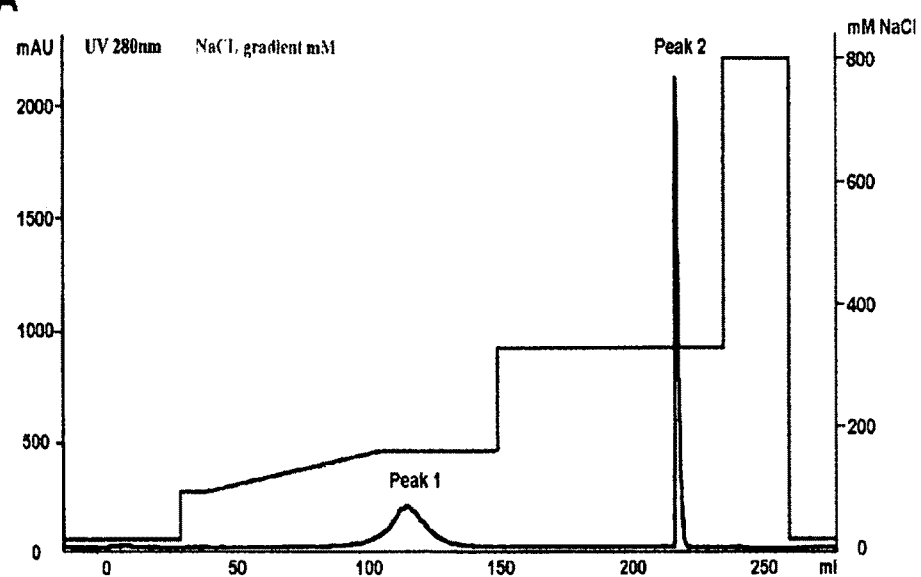

Official Action corresponding to European Patent Application No. 07 704 607.6-1222 dated Feb. 16, 2009.
Official Action corresponding to European Patent Application No. 07 704 607.6-1222 dated Sep. 14, 2009.
Rhodes et al., *A Formalin-Fixed, Paraffin-Processed Cell Line Standard for Quality Control of Immunohistochemical Assay of HER-2/neu Expression in Breast Cancer*. American Journal of Clinical Pathology. vol. 117 pp. 81-89 (2002).
Riesenberg et al., *Lysis of Prostate Carcinoma Cells by Trifunctional Bispecific Antibodies (αEpCAM x αCD3)*. The Journal of Histochemistry & Cytochemistry. vol. 49, No. 7 pp. 911-917 (2001).
Ruf, P., and Lindhofer, H., *Induction of a long-lasting antitumor immunity by a trifunctional bispecific antibody*. Blood. vol. 98, No. 8 pp. 2526-2534 (2001).
Sen et al., *Cutting Edge Communication: Use of Anti-CD2 X Anti-HER2/neu Bispecific Antibody for Redirecting Cytotoxicity of Activated T Cells Toward HER2/neu$^+$ Tumors*. Journal of Hematotherapy & Stem Cell Research. vol. 10 pp. 247-260 (2001).
Simoes et al., *Bi20 a new trifunctional bispecific antibody (CD20XCD3) in the treatment of resistance B cell tumors: First clinical data*. Blood. 45$^{th}$ Annual Meeting of the American Society of Hematology; San Diego, CA, USA; Dec. 6-9, 2003 [Abstract].
European Search Report corresponding to European Patent Application No. 10157479.6-1222 dated May 7, 2010.
Bernhard et al., "Induction of tumor-cell lysis by bi-specific antibody recognizing ganglioside GD2 and T-cell antigen CD3," International Journal of Cancer, vol. 55, No. 3 pp. 465-470 (Sep. 30, 1993).
Cochlovius et al., "Treatment of human B cell lymphoma xenografts with a CD3 x CD19 diabody and T-cells", J. Immunol., vol. 165, pp. 888-895 (2000).
De Gast et al., "Clinical experience with CD3 x CD19 bispecific antibodies in patients with B cell malignancies," J. Hematother., vol. 4, pp. 433-437 (1995).
Ginaldi et al., "Levels of expression of CD19 and CD20 in chronic B cell leukaemias," J. Clin. Pathol., vol. 51, p. 364 (1998).
Huh et al., "Higher levels of surface CD20 expression on circulating lymphocytes compared with bone marrow and lymph nodes in B-cell chronic lymphocytic leukemia," Am. J. Clin. Pathol., vol. 116, pp. 437-443 (2001).
Kipriyanov et al., "Synergistic antitumor effect of bispecific CD19 x CD3 and CD19 x CD16 diabodies in a preclinical model of non-Hodgkin's lymphoma," J. Immunol., vol. 169, pp. 137-144 (2002).
Lewis et al., "Differential responses of human tumor cell lines to anti-p185HER2 monoclonal antibodies," Cancer Immunol. Immunother., vol. 37, No. 4, pp. 255-263 (1993).
Lindhofer et al., "Bispecific antibodies target operationally tumor-specific antigens in two leukemia relapse models," Blood, vol. 88, pp. 4651-4658 (1996).
Loffler et al., "Efficient elimination of chronic lymphocytic leukaemia B cells by autologous T cells with a bispecific anti-CD19/anti-CD3 single-chain antibody construct," Leukemia, vol. 17, pp. 900-909 (2003).
Manzke et al., "Locoregional treatment of low-grade B-cell lymphoma with CD3xCD19 bispecific antibodies and CD28 costimulation. 1. Clinical phase I evaluation," Int. J. Cancer, vol. 91, pp. 508-515 (2001).
Manzke et al., "Locoregional treatment of low-grade B-cell lymphoma with CD3xCD19 bispecific antibodies and CD28 costimulation. II. Assessment of cellular immune responses," Int J. Cancer, vol. 91 pp. 516-522 (2001).
Official Action corresponding to European Patent Application No. 07 704 607.6-1222 dated Jun. 28, 2011.
Paik et al., "Real-world performance of HER2 testing—National Surgical Adjuvant Breast and Bowel Project experience," J. Natl. Cancer Inst., vol. 94, No. 11, pp. 852-854 (2002).
Ross et al., "HER-2/neu Testing in Breast Cancer," Am. J. Clin. Pathol., vol. 120, Suppl. 1, pp. S53-S71 (2003).
Ruf et al., "Two new trifunctional antibodies for the therapy of human malignant melanoma," International Journal of Cancer, vol. 108, No. 5, pp. 725-732 (Feb. 20, 2004).
Sarup et al., "Characterization of an anti-p185HER2 monoclonal antibody that stimulates receptor function and inhibits tumor cell growth," Growth Regul., vol. 1, No. 2, pp. 72-82 (1991).
Schmitt, et al., "Opsonization by the bispecific trifunctional antibody removab results in enhanced lysis of epcam+ squamous cell carcinoma of the upper aerodigestive tract," [Abstract]. Database accession No. PREV200300357979 and Blood vol. 100, No. 11 (Nov. 16, 2002). Page abstract No. 3708, 44th Annual Meeting of the American Society of Hematology, Philadelphia PA, USA, Dec. 6-10, 2002. ISSN 0006-4971.
Simoes et al., T Cell Response Against B Cell Tumor Lines Induced by BI20, a Novel Trifunctional Bispecific (CD20xCD3) Antibody. [Abstract]. Blood, vol. 100, No. 11 (Nov. 16, 2002). Page abstract No. 4789, XP009049081.
Smith, M. R., "Rituximab (monoclonal anti-CD20 antibody): mechanisms of action and resistance," Oncogene, vol. 22, pp. 7359-7368 (2003).
Weiner et al., "Bispecific monoclonal antibody therapy of B-cell malignancy," Leuk. Lymphoma, vol. 16, pp. 199-207 (1995).
Winkler et al., "Cytokine-release syndrome in patients with B-cell chronic lymphocytic leukemia and high lymphocyte counts after treatment with an anti-CD20 monoclonal antibody (rituximab, IDEC-C2B8)," Blood, vol. 94, pp. 2217-2224 (1999).
Withoff et al., "Characterization of BIS20x3, a bi-specific antibody activating and retargeting T-cells to CD20-positive B-cells," Br. J. Cancer, vol. 84, pp. 1115-1121 (2001).
Wollenberg et al., "Pilotstudy with a trifunctional bispecific antibody in patients with head and neck cancer," Eur J. of Cancer, Pergamon Press, Oxford, GB, vol. 37, p. S61 (Sep. 2001) XP027403892, ISSN:0959-8049.
Zeidler et al., "TNFalpha contributes to the antitumor activity of a bispecific, trifunctional antibody," Anticancer Res., vol. 21, No. 5, pp. 3499-3503 (2001).
Zeidler et al., "The Fc-region of a new class of intact bispecific antibody mediates activation of accessory cells and NK cells and induces direct phagocytosis of tumour cells," Br. J. Cancer, vol. 83, pp. 261-266 (2000).
Zeidler et al., "Simultaneous activation of T cells and accessory cells by a new class of intact bispecific antibody results in efficient tumor cell killing," J. Immunol., vol. 163, pp. 1246-1252 (1999).
"HercepTest™ for the DakoCytomation Autostainer," DakoCytomation Test Kit instructions, pp. 1-70 (Oct. 13, 2004).
Official Action corresponding to European Patent Application No. 07 704 607.6-11 dated Aug. 14, 2012).
Official Action corresponding to Japanese Patent Application No. 2008-554780 dated Jun. 27, 2012.
Stott et al., "Isolation of circulating tumor cells using a microvortex-generating herringbone-chip," vol. 107, No. 43, pp. 18392-18397 (Oct. 26, 2010).
Abstract No. 851449 of 33rd Annual San Antonio Breast Cancer Symposium (Dec. 8, 2012).
Arena et al., "Quantitative Flow Cytometry for the Differential Diagnosis of Leukemic B-Cell Chronic Lymphoproliferative Disorders," vol. 64, pp. 275-281 (2000).
European Search Report corresponding to European Patent Application No. 11154648.7-1222 / 2335729 dated Nov. 15, 2011.
Examination Report corresponding to Japanese Patent Application No. 2008-554780 dated Jun. 27, 2012.
Gastl et al., "Ep-CAM overexpression in breast cancer as a predictor of survival," The Lancet, vol. 356, pp. 1981-1982 (Dec. 9, 2000).
Gehrmann et al., "Dual function of membrane-bound heat shock protein 70 (Hsp70), Bag-4, and Hsp40: protection against radiation-induced effects and target structure for natural killer cells," Cell Death and Differentiation, vol. 12, pp. 38-51 (2005).
Golay et al., "CD20 levels determine the in vitro susceptibility to rituximab and complement of B-cell chronic lymphocytic leukemia: further regulation by CD55 and CD59," Blood, vol. 98, No. 12, pp. 3383-3389 (Dec. 1, 2001).

(56) References Cited

OTHER PUBLICATIONS

Jager et al., "The Trifunctional Antibody Ertumaxomab Destroys Tumor Cells That Express Low Levels of Human Epidermal Growth Factor Receptor 2," Cancer Res., vol. 69, No. 10, pp. 4270-4276 (May 15, 2009).

Leteurtre et al., "Differential mucin expression in colon carcinoma HT-29 clones with variable resistance to 5-fluorouracil and methotrexate," Biology of the Cell, vol. 96, pp. 145-151 (2004).

McKeage et al., "Trastuzumab—A Review of its Use in the Treatment of Metastatic Breast Cancer Overexpressing HER2," Drugs, vol. 62, No. 1, pp. 209-243 (2002).

Notice of Acceptance corresponding to Australian Patent Application No. 2007216472 dated Jan. 7, 2013.

Official Action corresponding to European Patent Application No. 11 154648.7-1403 dated Mar. 21, 2013.

Rao et al., "Expression of epithelial cell adhesion molecule in carcinoma cells present in blood and primary metastatic tumors," International Journal of Oncology, vol. 27, pp. 49-57 (2005).

Schuler et al., "First Results from a Phase Ib Study of the anti-EpCAM Antibody Adecatumumab (MT201) in Combination with Docetaxel in Patients with Metastatic Breast Cancer," ESMO Poster Stockholm (2008).

Spizzo et al., "High Ep-CAM expression is associated with poor prognosis in node-positive breast cancer," Breast Cancer Research and Treatment, vol. 86, pp. 207-213 (2004).

Official Action corresponding to Chinese Patent Application No. 200780012777.8 dated Jan. 5, 2013. (Translation).

Official Action corresponding to Canadian Patent Application No. 2,642,606 dated Mar. 8, 2013.

Decision of Refusal corresponding to Japanese Patent Application No. 2008-554780 dated Jan. 3, 2013. (Translation).

\* cited by examiner

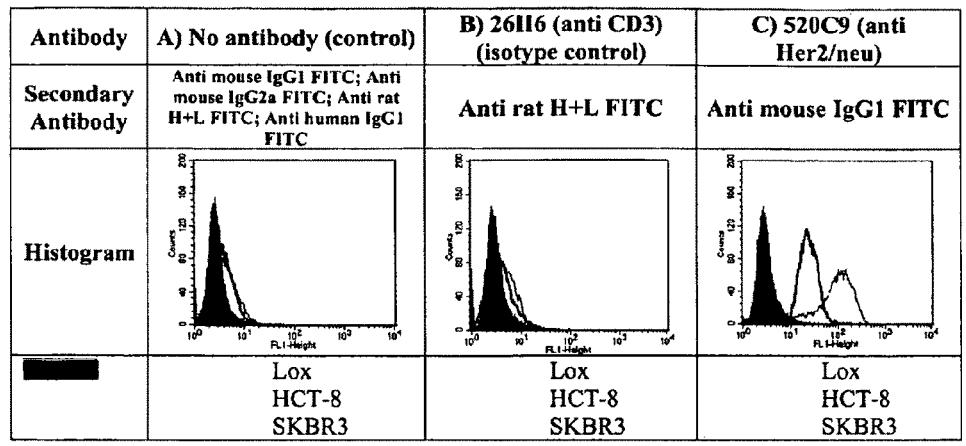
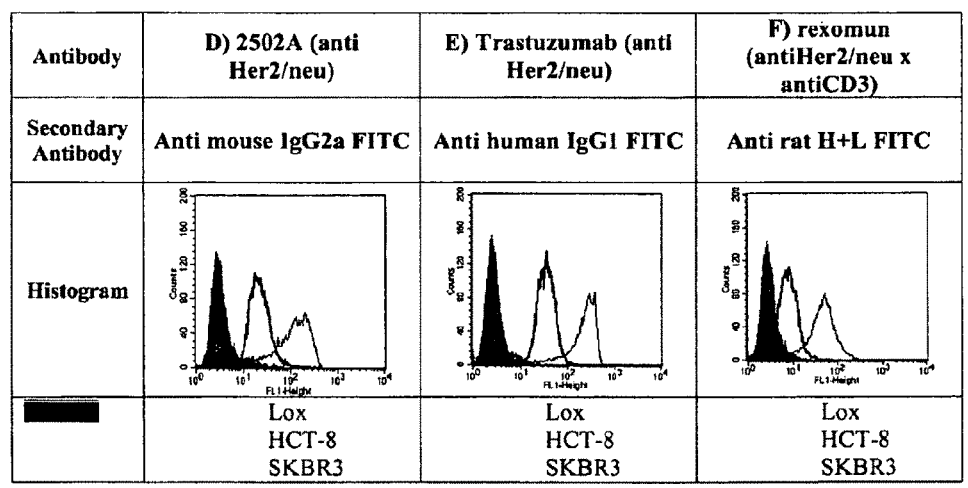
Figure 1: A-F Her2/neu expressing profiles of cell lines Lox, HCT-8 and SKBR3 with different anti Her2 antibodies measured by flow cytometry.

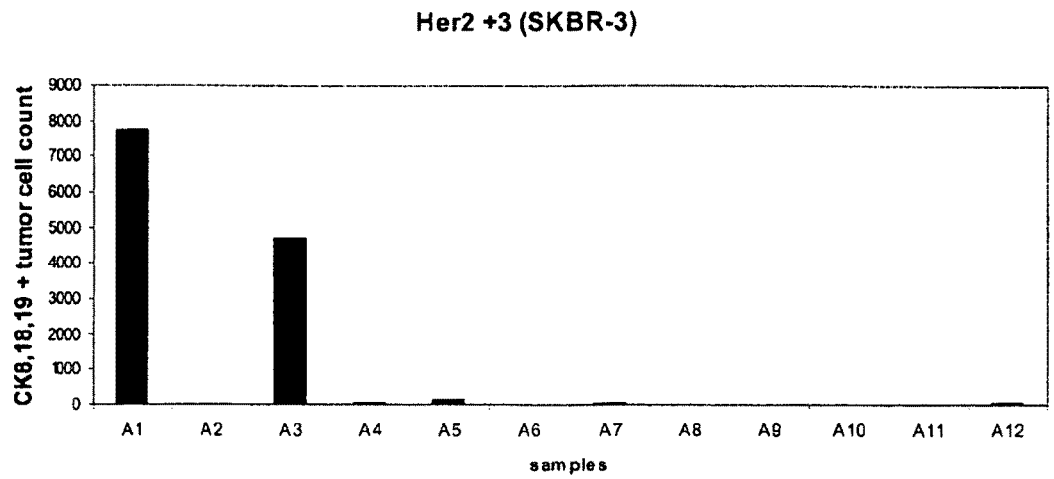

| *   | Her2 +3                        | donor 1 | donor 2 | donor 3 | Mean Value |
|-----|--------------------------------|---------|---------|---------|------------|
| A1  | SKBR-3                         | 2470    | 14939   | 5920    | 7776       |
| A2  | PBMC                           | 0       | 0       | 0       | 0          |
| A3  | PBMC + SKBR3                   | 12452   | 1682    | 0       | 4711       |
| A4  | PBMC+SKBR3+100 µg Trastuzumab  | 57      | 0       | n.d.    | 29         |
| A5  | PBMC+SKBR3+50 µg Trastuzumab   | 286     | 6       | n.d.    | 146        |
| A6  | PBMC+SKBR3+20 µg Trastuzumab   | 23      | 18      | n.d.    | 21         |
| A7  | PBMC+SKBR3+10 µg Trastuzumab   | 149     | 22      | 0       | 57         |
| A8  | PBMC+SKBR3+1 µg Trastuzumab    | 19      | 10      | 0       | 10         |
| A9  | PBMC+SKBR3+100 ng rexomun      | 0       | 0       | 0       | 0          |
| A10 | PBMC+SKBR3+50 ng rexomun       | 0       | 15      | n.d.    | 8          |
| A11 | PBMC+SKBR3+10 ng rexomun       | 0       | 0       | n.d.    | 0          |
| A12 | PBMC+SKBR3+1 ng rexomun        | 75      | 0       | 0       | 25         |

Figure 2a: Killing of Her2+3 SKBR-3 cells: Dotplot analysis with the Micrometastasis Detection System; * number corresponding to table 3

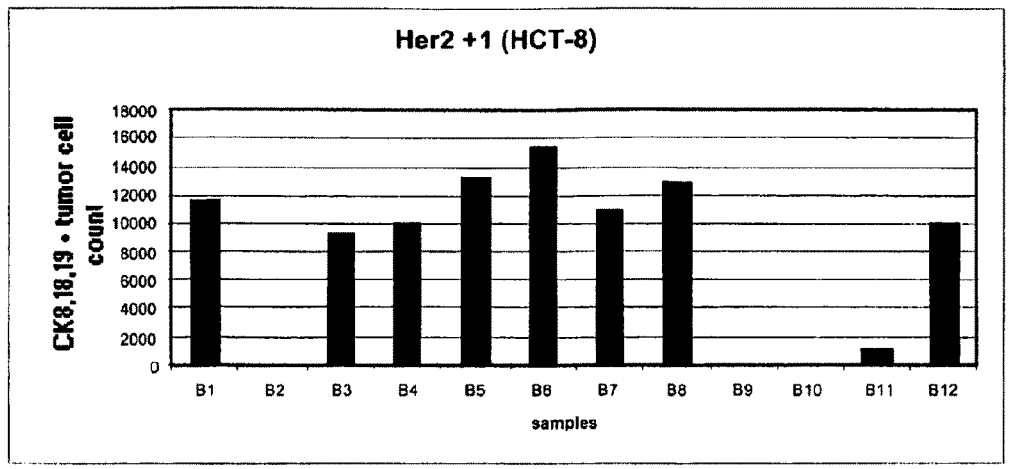

| *   | Her2 +1                      | donor 1 | donor 2 | donor 3 | Mean Value |
|-----|------------------------------|---------|---------|---------|------------|
| B1  | HCT-8                        | 12134   | 14460   | 8020    | 11538      |
| B2  | PBMC                         | 0       | 0       | 0       | 0          |
| B3  | PBMC + HCT-8                 | 8094    | 14031   | 5929    | 9351       |
| B4  | PBMC+HCT8+100 µg Trastuzumab | 14115   | 5640    | n.d.    | 9878       |
| B5  | PBMC+HCT8+50 µg Trastuzumab  | 12765   | 13530   | n.d.    | 13148      |
| B6  | PBMC+HCT8+20 µg Trastuzumab  | 16473   | 14020   | n.d.    | 15247      |
| B7  | PBMC+HCT8+10 µg Trastuzumab  | 18589   | 13676   | 179     | 10815      |
| B8  | PBMC+HCT8+1 µg Trastuzumab   | 20353   | 14325   | 3667    | ·12782     |
| B9  | PBMC+HCT8+100 ng rexomun     | 198     | 13      | 0       | 70         |
| B10 | PBMC+HCT8+50 ng rexomun      | 63      | 16      | n.d.    | 40         |
| B11 | PBMC+HCT8+10 ng rexomun      | 257     | 1778    | n.d.    | 1018       |
| B12 | PBMC+HCT8+1 ng rexomun       | 15199   | 12941   | 1542    | 9894       |

Figure 2b: Killing of Her2+1 HCT-8 cells: Dotplot analysis with the Micrometastasis Detection System; * numbers corresponding to table 3

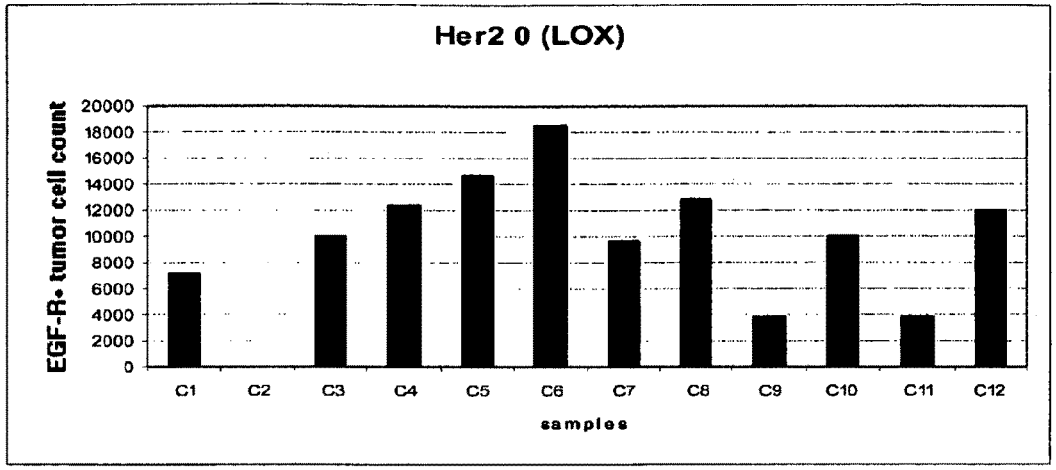

| *   | Her2 0                      | donor 1 | donor 2 | donor 3 | Mean Value |
|-----|-----------------------------|---------|---------|---------|------------|
| C1  | Lox                         | 10334   | 10334   | 852     | 7173       |
| C2  | PBMC                        | 0       | 0       | 0       | 0          |
| C3  | PBMC + Lox                  | 4387    | 23096   | 2740    | 10074      |
| C4  | PBMC+Lox+100 µg Trastuzumab | 6611    | 17992   | n.d.    | 12302      |
| C5  | PBMC+Lox+50 µg Trastuzumab  | 9758    | 19623   | n.d.    | 14691      |
| C6  | PBMC+Lox+20 µg Trastuzumab  | 11730   | 25364   | n.d.    | 18547      |
| C7  | PBMC+Lox+10 µg Trastuzumab  | 4745    | 20176   | 4287    | 9736       |
| C8  | PBMC+Lox+1 µg Trastuzumab   | 3267    | 28197   | 6980    | 12815      |
| C9  | PBMC+Lox+100 ng rexomun     | 8712    | 2488    | 332     | 3844       |
| C10 | PBMC+Lox+50 ng rexomun      | 7859    | 11978   | n.d.    | 9919       |
| C11 | PBMC+Lox+10 ng rexomun      | 4202    | 3469    | n.d.    | 3836       |
| C12 | PBMC+Lox+1 ng rexomun       | 5674    | 22853   | 7313    | 11947      |

Figure 2c: Killing of negative Her2 Lox cells: Dotplot analysis with the Micrometastasis Detection System; * numbers corresponding to Table 3

| * | Sample | Tumor cell count | Dotplot | * | Sample | | Dotplot |
|---|---|---|---|---|---|---|---|
| B1 | HCT-8 | 14460 | 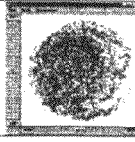 | B7 | PBMC + HCT-8 + 10 µg Trastuzumab | 13676 | 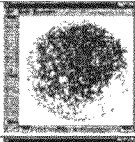 |
| B2 | PBMC | 0 | No tumor cells detectable | B8 | PBMC + HCT-8 + 1 µg Trastuzumab | 14325 | 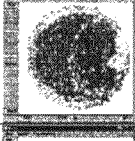 |
| B3 | PBMC + HCT-8 | 14031 | 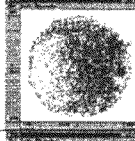 | B9 | PBMC + HCT-8 + 100 ng rexomun | 13 | |
| B4 | PBMC + HCT-8 + 100 µg Trastuzumab | 5640 |  | B10 | PBMC + HCT-8 + 50 ng rexomun | 16 | 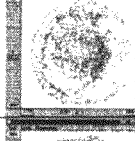 |
| B5 | PBMC + HCT-8 + 50 µg Trastuzumab | 13530 |  | B11 | PBMC + HCT-8 + 10 ng rexomun | 1778 | 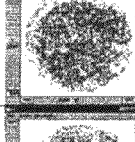 |
| B6 | PBMC + HCT-8 + 20 µg Trastuzumab | 14020 |  | B12 | PBMC + HCT-8 + 1 ng rexomun | 12941 | 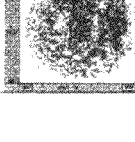 |

Figure 2d: Killing of Her2 1+ HCT-8 cells; Dotplot results of donor 2 as an example for the MDS workflow; * numbers corresponding to table 3

| Supernatant from | pg/ml IFN-g (1:50) | pg/ml TNF-a (1:50) | pg/ml IL-10 (1:1) | pg/ml IL-6 (1:50) | pg/ml IL-4 (1:1) | pg/ml IL-2 (1:1) |
|---|---|---|---|---|---|---|
| PBMC | 0 | 0 | 19 | 553 | 0 | 2 |
| PBMC + HCT-8 | 773 | 261 | 1545 | 22102 | 10 | 0 |
| PBMC + HCT-8 + 50µg Trastuzumab | 0 | 269 | 1981 | 27466 | 5 | 0 |
| PBMC + HCT-8 + 100 ng Trastuzumab | 1617 | 571 | 1703 | 32259 | 0 | 1 |
| PBMC + HCT-8 + 100 ng rexomun | 52479 | 4499 | 4135 | 40740 | 121 | 703 |
| PBMC + HCT-8 + 1 ng rexomun | 0 | 433 | 1780 | 23694 | 71 | 2 |

Figure 3: Cytokine secretion in clongenic assay supernatants after 24 h measured with the Cytokine Bead Array system (CBA)

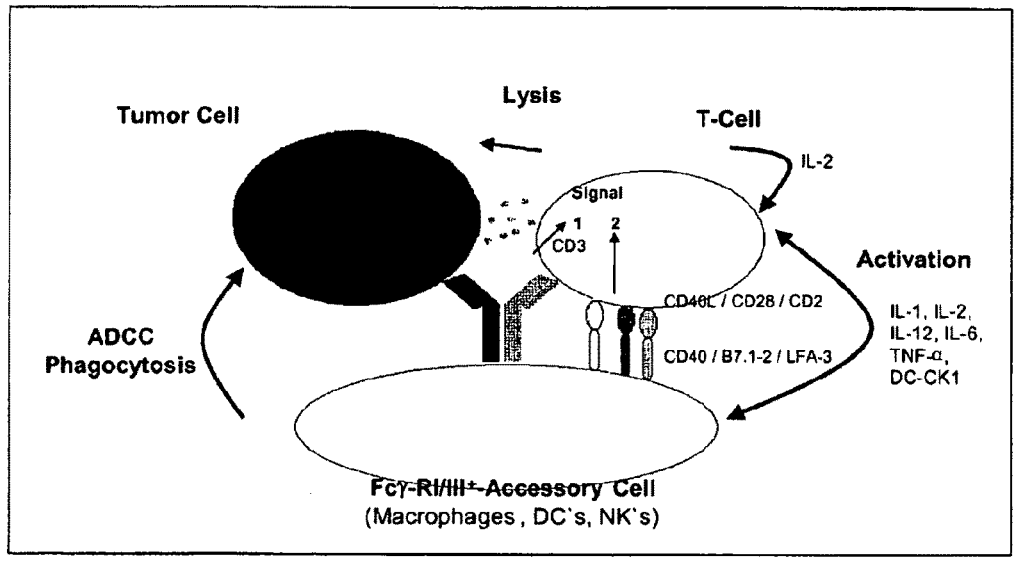

Figure 4: The postulated tri-cell-complex. The trifunctional antibody is able to accelerate the recognition and destruction of tumour cells by different immunological mechanisms.
Note: ADCC, Antibody dependent cellular cytotoxicity; DC, Dendritic cell; NK, Natural killer cell; DC-CK1, Dendritic cell cytokine 1; IL, Interleukin; LFA, Leukocyte function associated antigen; TNF-α, Tumor necrosis factor α; CD, Cluster of differentiation (adapted from Ruf&Lindhofer, 2001)

DESTRUCTION OF TUMOR CELLS BY TRIFUNCTIONAL BISPECIFIC ANTIBODIES WITH LOW TO MEDIUM EXPRESSION LEVELS OF TUMOR-ASSOCIATED TARGET ANTIGENS

The present invention refers to the use of trifunctional bispecific antibodies for the preparation of a pharmaceutical composition for the prophylaxis and treatment of tumor diseases.

A hitherto unsolved problem in the treatment of tumors by monospecific monoclonal antibodies during an immune therapy is the insufficient efficiency of tumor cell destruction with low to medium expression levels of tumor target antigens. One particular example is the treatment of breast cancer with a low to medium expression level of the target antigen Her2/neu; another particular example is the treatment of non-Hodgkin's lymphoma and chronic lymphatic leukemia with low expression of CD20 tumor antigen.

Metastatic breast cancer is an almost always fatal disease. The median survival time from first manifestation of metastases ranges from 17 to 20 months. A number of endocrine, cytotoxic and biological agents have demonstrated palliative efficacy but there is no consensual standard of care, and treatment often causes substantial adverse effects.

Epidermal growth factor (EGF) family member Her2/neu is overexpressed in tumor specimens of approximately 25-30% of breast cancer patients and attributed to more aggressive tumor growth and a worse prognosis.

The family of EGF receptors includes four members EGFR (ERBB1), Her2/neu (ERBB2), ERBB3 and ERBB4. EGFR and Her2/neu have been intensely pursued as therapeutic targets. Antibodies targeting the extra cellular domain of EGFR and Her2/neu as well as small molecular compounds inhibiting intracellular receptor signalling are already in clinical use and have demonstrated clinical efficacy. However, their anti-tumor effects are often not as strong as predicted from pre-clinical studies and combination with chemotherapy is preferable.

HERCEPTIN® is a well-accepted monoclonal antibody widely used for the treatment of breast cancer; however, HERCEPTIN® can be successfully used only for patients with an expression level of the target antigen Her2/neu of at least 2+/FISH+ (as verified by the so-called HERCEPTEST® and a positive FISH-analysis) or 3+ on their tumor cells. Several studies have shown that a relatively high expression density of the target antigen Her2/neu with an additional gene amplification of Her2/neu (being reflected by a positive FISH test) is necessary in order to obtain a statistically significant survival. Pre-clinical in vitro experiments have also shown that an efficient destruction of tumor cells by HERCEPTIN® is visible only when tumor cells express a high level of the target antigen Her2/neu.

These limitations are responsible that only about 25-30% of the patients with metastatic breast cancer which express high levels of Her2/neu on their tumors (scored as 2+/FISH+ or 3+ with the Dako HERCEPTEST®) can be efficiently treated with HERCEPTIN®.

In a study of Perez and co-workers, 35% of breast cancer patients were scored as Her2 1+, 14% as 2+, and 13% as 3+ evaluated with immunohistochemistry (IHC) (Perez E A et al.: Her2 testing in patients with breast cancer: poor correlation between weak positivity by immunohistochemistry and gene amplification by fluorescence in situ hybridization. Mayo Clin Proc 2002; 77: 148-154)

Kiewe, P. et al.: "Phase I trial of the trifunctional anti-Her2×anti-CD3 antibody ertumaxomab in metastatic breast cancer"; Journal of Clinical Oncology, vol 23, no. 16S, 1 Jun. 2005 (ASCO Abstract 2205-06-01) describe the use of an intact bispecific monoclonal antibody targeting Her2/neu and CD3. This antibody was used in a phase I trial in treating metastatic breast cancer. In order to study any side effects caused by this anti-Her2/neu×anti-CD3 antibody and in order to accelerate recruiting the necessary number of 17 patients, patients with the HERCEPTEST® score 1+ (25%), 2+ (12.5%) and 3+ (62.5%) were tested. An antitumor response was seen in 4 out of 15 evaluable patients at this preliminary outcome analysis. However, none of these patients falling within the HERCEPTEST® score 1+ showed an antitumor response. No information at all is given concerning the Her2/neu expression status of these responders. Additionally, at the time of the design of this phase I study, only experimental data were available that ertumaxomab eliminates cell lines (e.g. Sk-Br-3) expressing high levels (3+ score) of Her2/neu.

As in all typical phase I trials, the phase I trial of Kiewe et al. was designed to investigate the safety and tolerability of the trifunctional antibody ertumaxomab. Secondary variables in this trial were antitumor activity and measurement of different immunological parameters. To speed up patient recruitment into this study, no restrictions were taken regarding the expression of Her2/neu on the patients' tumor cells. This was possible, since the primary objectives for this study were safety and tolerability while the level of Her2/neu expression on tumor cells was of no importance at all.

The finding that the trifunctional antibody anti-HER2×anti-CD3 ertumaxomab seemed to be effective only in patients overexpressing Her2/neu in accordance with scores 2+ and 3+ was not surprising at all as also other investigations performed with antibodies like HERCEPTIN® showed efficiency only for patients expressing Her2/neu at medium (2+/FISH+) to high levels (3+).

For instance Gatzemeier et al., Anals of Oncology 15:19-27, 2004 provided evidence that antibodies like HERCEPTIN® do provide clinical benefit only for patients within 3+ or 2+/FISH+ expression of Her2/neu.

Similarly, Micromet, Inc. published on Oct. 2, 2006 data on 2 phase II trials with adecatumumab, an antibody directed against the epithelial cell adhesion molecule EpCAM in breast and prostate cancer. Only patients expressing high levels of EpCAM on their tumor tissue showed a significant prolongation of time-to-progression while patients with a low EpCAM expression showed no significant benefit. It was emphasized that adecatumumab may offer a treatment option for patients with breast cancers highly overexpressing EpCAM. It was not found to be useful at all for patients with low overexpression of EpCAM.

Non-Hodgkin's lymphoma (NHL) and chronic lymphocytic leukemia (CLL) are among the most prevalent malignancies. NHL is the fifth most common malignant disease in the United States with an annual incidence rate of 18-20/100,000 individuals. The incidence of NHIL increased annually by 5-10%[1] until the mid-1990s but has remained constant since then.[2] CLL is the most common leukemia in the Western world with an annual incidence of 3-4/100,000 individuals.

Despite promising results in the treatment of B-cell lymphomas using the anti-CD20 monoclonal antibody Rituximab (especially in combination with chemotherapy), patients eventually relapse.[9,35] Therefore, there is a need for further therapeutic options.

Currently, both indolent NHL and CLL are incurable diseases, despite the fact that major improvements in therapy were achieved after the approval of monoclonal antibodies like Rituximab and alemtuzumab.[3-6] Although antibody monotherapy has not been highly successful, particularly in CLL the combination of a monoclonal antibody with a standard chemotherapy regimen significantly improved patients' outcomes.[7,8] However, patients eventually relapse,[9] and new therapeutic strategies are desperately sought. Many new drug candidates such as fully humanized anti-CD20 antibodies or antibodies targeted against other antigens (e.g., CD19, CD22, CD23, CD80, or HLA-DR) are currently under intensive investigation.[10,11]

In addition to the search for new targets, another approach to improving antibody therapy was the development of bispecific antibodies. Various bispecific formats have been developed and tested, e.g., full-length antibodies produced in quadroma cells, chemically crosslinked F(ab)$_2$ fragments, single chain antibodies,[12] and diabodies.[13] Some of these antibodies have been tested for treatment of human lymphomas. However, despite promising in vitro efficacy, these molecules showed only limited clinical benefit.[14-16]

Bispecific antibodies directed against B-cell-specific antigens such as CD19 or CD20 have been under intensive investigation for the last 10-15 years, but limited clinical data showing only moderate responses[14,36,37] are available thus far. Moreover, the complicated and inefficient manufacturing process makes it difficult to produce sufficient amounts of antibody for clinical use.

Bispecific antibodies (bsAb) are tools for immunological treatment of e.g. malignant cells by redirecting effector cells against tumor cells. However, bsAbs normally redirect and activate only a single class of effector cells, i.e., either T-cells, NK-cells, FcγRI$^+$, or FcαRI$^+$ cells, thereby limiting their efficacy. All of these prior art antibodies have been described to efficiently treat tumors only when the tumor-associated antigens are expressed at a medium to high level on the tumor cell surface.

Enhancing immunological effector functions of antibodies reflects one approach to improve the efficacy of antibody-based cancer therapy. Trifunctional bispecific antibodies with improved effector functions have been described by the present authors, for instance in the publications of Zeidler et al.[18] Riesenberg et al.[22] Ruf & Lindhofer[20] or Heiss et al.,[21] recognizing not only tumor cells and T lymphocytes with its two binding arms, but also binding Fcγ-receptor positive accessory cells through their Fc-region. However, also these antibodies had not been known up to now to be useful in the treatment of tumor cells expressing tumor-associated antigens like Her2/neu or CD20 at a low level.

The limitations explained above for Her2/neu, EpCAM and CD20 are also valid for other tumor-associated antigens like e.g. G250, GD3, GD2, proteoglycans, MHC II, EGF-R and CEA.

Summarizing, all experimental data available up to the priority date of the present invention provided only evidence of significant benefits for patients with a medium to high overexpression of the tumor antigen.

Therefore, there is a need for improvement of antitumor activity of antibodies which can also kill e.g. Her2/neu low expressing tumor cells (scored e.g. as 1+ with the Dako HERCEPTEST®) or an expression of Her2/neu at a medium level of up to 500,000 tumor-associated antigens/tumor cells and scored as 2+ with the Dako HERCEPTEST® but FISH negative, or CD20 low expressing tumor cells or such tumor cells expressing one or more of the above specified tumor-associated antigens at a level and in a range which covers about 1,000-350,000, particularly 5,000 to 150,000 tumor-associated antigens/tumor cells, particularly for CD20 and EpCAM.

The above described problem has been found to be solved by antibodies facilitating a cooperation of different classes of immune cells selected from trifunctional bispecific antibodies having the following properties:
  (a) binding to a T cell;
  (b) binding to at least one tumor-associated antigen on a tumor cell, said antigen being selected from the group consisting of Her2/neu, CD20, EpCAM, G250, GD3, GD2, proteoglycans, MHC II, EGF-R and CEA;
  (c) binding via their Fc-portion to Fcγ-receptor type I and/or III positive cells;
  for the preparation of a pharmaceutical composition for the prophylaxis and treatment of tumor diseases wherein said tumor-associated antigen is expressed on said tumor cell
    in an amount of about 5,000-about 150,000 tumor-associated antigens/tumor cell for Her2/neu, or
    in an amount of about up to 500,000 tumor-associated antigens/tumor cell for Her2/neu in tumor cells tested FISH negative, or
    in an amount of about 1,000 to about 350,000 tumor-associated antigens/tumor cell for CD20, or
    in an amount of about 1,000 to about 350,000 preferably of up to about 300,000 tumor-associated antigens/tumor cell for EpCAM, G250, proteoglycans, GD2, GD3, MHC II, EGF-R and CEA.

In one embodiment of the invention, all recited tumor antigens are expressed on the tumor cell in an amount of about 5,000 to about 150,000 tumor-associated antigens/tumor cell.

The present invention provides also a method for the treatment of humans or animals for the prophylaxis and treatment of tumor diseases by contacting the humans' or animals' tumor cells containing bodies or parts of these bodies containing said tumor cells with a pharmaceutically effective amount of trifunctional bispecific antibodies having the following properties:
  (a) binding to a T cell;
  (b) binding to at least one tumor-associated antigen on a tumor cell, said antigen being selected from the group consisting of Her2/neu, CD20, EpCAM, G250, GD3, GD2, proteoglycans, MHC II, EGF-R and CEA;
  (c) binding via their Fc-portion to Fcγ-receptor type I and/or III positive cells;
  wherein said tumor-associated antigen is expressed on said tumor cell
    in an amount of about 5,000-about 150,000 tumor-associated antigens/tumor cell for Her2/neu, or
    in an amount of about up to 500,000 tumor-associated antigens/tumor cell for Her2/neu in tumor cells tested FISH negative, or
    in an amount of about 1,000 to about 350,000 tumor-associated antigens/tumor cell for CD20, or
    in an amount of about 1,000 to about 350,000 preferably of up to about 300,000 tumor-associated antigens/tumor cell for EpCAM, G250, proteoglycans, GD2, GD3, MHC II, EGF-R and CEA.

The said contacting of said trifunctional bispecific antibodies with the patients' tumor cells is either performed by administering the trifunctional bispecific antibodies in any acceptable dosage form either orally or parenterally as described below into the humans' or animals' body.

Provided that tumor diseases like leukemias or lymphomas involving cells of the immune system are to be treated, said contacting can also be performed ex vivo. Reference is made for instance to U.S. Pat. No. 7,018,632 or U.S. Pat. No. 5,985,276, which are fully incorporated herein by reference.

The autologous tumor cells containing material is incubated with the trifunctional bispecific antibodies described herein either during a short-term incubation for a period of 10 minutes to 10 hours, preferably up to 5 hours, or in a long-term incubation also for a period of time as described for the short-term incubation, so that the autologous tumor cells are charged with their antibodies. Subsequently, blood cells of the patient, preferably mononucleated cells of the peripheral blood (PBMC) are added, and this mixture is then incubated over a long period, such as 1 to 14 days. Alternatively, the autologous tumor cells are directly contacted with said trifunctional bispecific antibodies and with the patients' blood cells, preferably peripheral blood mononucleated cells. In this way, "priming" of numerous immune cells against the tumor is achieved already ex vivo. Afterwards, these cells are re-infused into the patient. Long-term incubation also leads to internalization and degradation of the antibodies. As described above, the above cited US patents fully describe these methods; however, no reasonable expectation of success at all is provided for the expert that it might also be possible to treat tumor diseases involving tumor cells with an expression of about 5,000 to about 150,000 tumor-associated antigens per tumor cell for the above-indicated tumor-associated antigens. The methods may be performed in allogeneic or autologous settings without additional healthy donor PBMCs. Remarkably, the depletion of tumor cells, particularly B-cells, is not dependent on any pre- or co-activation of the effector cells with cytokines (e.g., IL-2, GM-CSF) which is a typical disadvantage for other bispecific or monospecific antibodies described in the art.

Preferred embodiments of the invention are indicated in the subclaims as well as in the following description and the accompanying experimental data, figures and tables.

The present inventors could surprisingly show that trifunctional bispecific antibodies already described in the art can be efficiently used for targeting particularly selected tumor-associated target antigens on a tumor cell which are expressed on said tumor cell to an only low to medium level. Particularly preferred are Her2/neu, EpCAM and CD20 tumor-associated antigens as target antigens.

The tumor-associated antigens are expressed on the tumor cells in different levels depending on the type of tumor-associated antigen expressed on said tumor cell and whether or not the tumor antigen is amplified in case of Her2/neu.

It has been found that patients can be successfully treated with the trifunctional bispecific antibodies as described herein if their tumors express Her2/neu on a tumor cell in an amount of about 5000 to about 150,000 tumor-associated antigens per tumor cell in the case of Her2/neu. These patients will be scored as 1+ in accordance with the DAKO HERCEPTEST®. At may also be correct to classify the upper limit for 1+ to about 100,000 or 110,000. Most importantly, the score has to classified as "low expression" contrary to "medium expression".

It has also been found that patients which express up to 500,000 molecules of Her2/neu tumor-associated antigens per tumor cell and which are classified as 2+ in accordance with the DAKO HERCEPTEST® can be successfully treated even if they are classified FISH negative. Up to now, only those patients could be successfully treated which were scored with a Her2/neu value of 2+ in accordance with the DAKO HERCEPTEST® expressing up to 500,000 Her2/neu tumor antigens per tumor cell but being FISH positive. FISH negative patients with a Her2/neu value of 2+ could not be successfully treated.

In patients with tumors expressing CD20, it has been surprisingly found that they can be successfully treated even if the expression of CD20 is in an amount about 1000 to about 350,000 tumor-associated antigens per tumor cell. Additionally, patients with an expression of EpCAM, G250, proteoglycans, GD2, GD3, MHC II, EGF-R and CEA in an amount of about 1000 to about 350,000 tumor-associated antigens per tumor cell can be successfully treated with the trifunctional bispecific antibodies described herein.

The tumor-associated antigens are expressed on the tumor cells preferably in amount of at least about 10,000, about 20,000, about 50,000 or about 80,000 tumor-associated antigens/tumor cell and preferably at a maximum of about 110,000, of about 120,000 or of about 130,000 tumor-associated antigens/tumor cell in case of Her2/neu.

For patients which are scored with the DAKO HERCEPTEST® with a Her2/neu value of 2+(medium expression), the preferred expression of tumor-associated antigens on the tumor cells is in an amount of up to 500,000 or up to 450,000, 400,000, 350,000, or 300,000 and with the lower limits of about 100,000, of more than about 110,000, with more than about 150,000, of about 200,000 or of about 250,000.

In tumor cells with an expression of CD20 tumor antigen, the number of CD20 molecules per tumor cell varies in a range of about 1000 to about 350,000, preferably up to about 310,000 or 300,000 dependent on the type of B-cell malignancy and the site in the body. The number of CD20 molecules per tumor cell can particularly vary from about 5000, about 10,000, about 50,000 to about 100,000, 150,000, 200,000, 250,000 up to 300,000. The situation is similar for all other tumor antigens indicated in claim 1 being EpCAM, G250, proteoglycans, GD2, GD3, MHC II, EGF-R and CEA.

It should be noted that the expression levels of tumor-associated antigens could range between the lower and upper expression values on different tumor cells originating from a single defined tumor entity. It has to be understood that all of these figures are mean values depending on the type of malignancy, the type of patient, the progression of the tumor etc.

It is quite important to note that the tumor-associated target antigens selected by the present inventors are permanently and stably expressed on the tumor cell with low to medium expression levels only. While other type of inducible antigens like heat shock proteins and the MIC molecules MIC A and MIC B, which are both under the control of heat shock promoter elements, are expressed after induction with increasing levels during lifetime, the expression rate of tumor-associated antigens like Her2/neu and CD20 is generally constant and stable.

The tumor-associated antigens selected by the present inventors are associated with or specific for particular tumors. EpCAM is typically associated with adenocarcinomas, Her2/neu with mammary carcinomas but also with colon, lung, gastric, pancreas and ovarian cancer, CD20 with B cell lymphomas like non-Hodgkin's lymphoma or chronic lymphotic leukemia, G250 with renal carcinomas, proteoglycans, GD3 and GD2 with melanomas, MHC II with B cell lymphomas and EGF-R and CEA with epithelial tumors.

The trifunctional bispecific antibodies (shortly trAb) used in the present invention are known per se. Reference is made for instance to U.S. Pat. No. 6,551,592 the content of which is fully incorporated herein by reference. The same is true for DE-A-196 49 223 and DE-A-197 10 495, which are also included herein by reference together with their corresponding US patent documents.

The antibodies for use in the invention may be administered orally in any acceptable dosage form such as capsules, tablets, aqueous suspensions, solutions or the like. The antibodies and derivatives thereof may also be administered parenterally. That is via the following routes of administration: subcutaneous, intravenous, intraperitoneal, intramuscular, intra-articular, intra-synovial, intrasternal, intranasal, topical, intrathecal, intrahepatic, intratumoral, intralesional, and intracranial injection or infusion techniques. Generally, the antibodies will be provided as an intravenous injection or infusion.

The antibodies of the invention may be administered alone or with a pharmaceutically acceptable carrier, including acceptable adjuvants, vehicles, and excipients. All of these are familiar for those skilled in the art.

The effective dosage will depend on a variety of factors and it is well within the purview of a skilled physician to adjust the dosage for a given patient according to various parameters such as body weight, the goal of treatment, the highest tolerated dose, the specific formulation used, the route of administration, the response of the patient and the like.

The trAbs employed according to the present invention are preferably administered in an amount of about 5-about 1000 µg, further preferred about 10-about 300 µg, about 10-about 100 µg or about 10-about 50 µg, each per infusion. The optimal amounts may be determined by the skilled artisan by means of experimentation. Further preferred, the trifunctional antibody is used in an amount of about 0.05-about 15 µg/kg, further preferred about 0.5-5 µg/kg and about 0.5-2 µg/kg body weight. The number of administrations can be selected by the physician in accordance with the patient's need, particularly the severity of the disease, the patient's response, the dose applied and other various factors known in the art.

Preferably, said trifunctional antibody is selected to be an anti-CD3×anti-tumor-associated antigen antibody and/or anti-CD4×anti-tumor-associated antigen antibody and/or anti-CD5×anti-tumor-associated antigen antibody and/or anti-CD6×anti-tumor-associated antigen antibody and/or anti-CD8 anti-tumor-associated antigen antibody and/or anti-CD2×anti-tumor-associated antigen antibody and/or anti-CD28×anti-tumor-associated antigen antibody and/or anti-CD44×anti-tumor-associated antigen antibody, wherein particularly preferred an anti-CD3×anti-tumor-associated antigen antibody is used. Particularly preferred as the anti-tumor-associated antigen is a Her2/neu, EpCAM or CD20 antigen, further preferably combined with an anti-CD3 binding arm of the trifunctional antibody.

By using the trifunctional antibodies of the present invention, the Fc-receptor positive cells are activated by binding of the Fc-portion of the trAb to the Fc-receptor positive cell. Thereby, the expression of cytokines and/or co-stimulatory antigens is initiated or increased. Then, at least a second activation signal required for physiological activation of the T cell is transferred to said T cell by said co-stimulatory antigens and/or cytokines. This activation is indicated by up-regulation of activation markers, the killing of tumor cells and by the proliferation of T cells.

Activation of the Fc receptor-positive cell by the trAb is dependent on the subclass or the subclass combination of the antibody heavy chain fragments, respectively. As demonstrated by in vitro experiments, for example, trAbs of the mouse-IgG2a/rat-IgG2b subclass combination are able to bind to, and simultaneously activate, Fc receptor-positive cells leading to an up-regulation or new formation (expression), respectively, of co-stimulatory antigens such as CD40, CD80, or CD86 on the surface of these cells, while bispecific antibodies of the mouse-IgG1/rat-IgG2b subclass combination are able to bind to Fc receptor-positive cells ((1) Haagen et al., J. Immunology, 1995, 154: 1852-1860) but obviously are unable to activate these cells to a comparable extent ((2) Gast et al., Cancer Immunol. Immunother., 1995, 40: 390). Hence, mouse-IgG2a/ratIgG2b isotype combination in the Fc-region of the trAb is particularly preferred. However, this is also true for all other isotype combinations as recited in the present description so that they can be used in other preferred embodiments of the invention.

While the trAb simultaneously binds to and activates the T cell with one binding arm (e.g., anti-CD3), co-stimulatory signals from the Fc receptor-positive cell bound to the Fc portion of the trAb may be transferred to the T cell, i.e., only the combination of T cell activation via one binding arm of the trAb and simultaneous transfer of co-stimulatory signals from the Fc receptor-positive cell to the T cell leads to an efficient T cell activation.

Another important aspect in the induction of an anti-tumor immunity is the possible phagocytosis, processing and presentation of tumor components by the accessory cells (monocytes, macrophages, NK cells or dendritic cells) which have been targeted by the trAb. By this classical mechanism of antigen presentation both tumor-specific CD4− as well as CD8-positive cells may be generated. Moreover, tumor-specific CD4 cells play an important role in the induction of a humoral immune response in the context of T/B cell cooperation.

Trifunctional bispecific antibodies are able to bind to the T cell receptor complex of the T cell with one binding arm and to said tumor-associated antigens on the tumor cell with the second binding arm. Thereby, they activate T cells which destroy the tumor cells by releasing cytokines or by apoptosis-mediating mechanisms. Moreover, there seems to be the possibility that in the frame of activation by trifunctional antibodies T cells which recognize tumor-specific antigens via their receptor may be re-activated, whereby leading to a long-lasting antitumor immunity. Of particular importance in this respect is the intact Fc portion of the trifunctional bispecific antibody mediating the binding to accessory cells such as monocytes/macrophages and dendritic cells and causing them to develop cytotoxicity themselves and/or concomitantly transfer important co-stimulatory signals to the T cell.

Obviously, in this manner a T cell response may be induced against tumor-specific peptides which have been unknown up to now.

By redirecting possibly anergized tumor-specific T cells to tumor cells by means of trAbs and simultaneous co-stimulation of such T cells by accessory cells binding to the Fc portion of the trAb the anergic state of tumor-specific cytotoxic T cells (CTLs) could be abolished. I.e., a preexisting T cell tolerance existing in the patient against the tumor may be abolished by means of trAbs and, thus, a long-lasting anti-tumor immunity may be induced besides the direct destruction of the tumor cell.

Preferably, the antibodies employed according to the present invention are capable of reactivating tumor-specific T cells being in a state of anergy. Furthermore, they are capable of inducing tumor-reactive complement-binding antibodies and therefore to induce a humoral immune response.

Binding to the T cell preferably takes place via CD3, CD2, CD4, CD5, CD6, CD8, CD28, and/or CD44. The Fc receptor-positive cells have at least one Fcγreceptor I or III.

Antibodies which may be employed according to the present invention are able to bind to monocytes, macrophages, dendritic cells, "natural killer" cells (NK cells) and/or activated neutrophils being Fcγ receptor I and/or III-positive cells.

The antibodies which may be employed according to the invention lead to the initiation or increase of the expression of CD40, CD80, CD86, ICAM-1, and/or LFA-3 being co-stimulatory antigens, or/and secretion of cytokines by the Fc receptor-positive cell. Preferably, the cytokines are IL-1, IL-2, IL-4, IL-6, IL-8, IL-12, IFN-γ and/or TNF-α.

Preferably, binding to the T cell takes place via the T cell receptor complex of the T cell.

Preferably, the trifunctional bispecific antibody is a heterologous intact rat/mouse bispecific antibody.

By means, of the trAbs which may be used according to the present invention, T cells are activated and redirected against the tumor cells. Preferred useful heterologous trifunctional bispecific antibodies are selected from one or more of the following combinations of isotypes:
rat-IgG2b/mouse-IgG2a,
rat-IgG2b/mouse-IgG2b,
rat-IgG2b/mouse-IgG3;
rat-IgG2b/human-IgG1,
rat-IgG2b/human-IgG2,
rat-IgG2b/human-IgG3 [oriental allotype G3m(st)=binding to protein A],
rat-IgG2b/human-IgG4;
rat-IgG2b/rat-IgG2c;
mouse-IgG2a/human-IgG3 [caucasian allotypes G3m(b+g)=no binding to protein A, in the following indicated as *]
mouse-IgG2a/mouse-[VH-CH1,VL-CL]-human-IgG1-[hinge]-human-IgG3*-[CH2-CH3]
mouse-IgG2a/rat-[VH-CH1,VL-CL]-human-IgG1-[hinge]-human-IgG3*-[CH2-CH3]
mouse-IgG2a/human-[VH-CH1,VL-CL]-human-IgG1-[hinge]-human-IgG3*-[CH2-CH3]
mouse-[VH-CH1,VL-CL]-human-IgG1/rat-[VH-CH1,VL-CL]-human-IgG1-[hinge]-human-IgG3*-[CH2-CH3]
mouse-[VH-CH1,VL-CL]-human-IgG4/rat-[VH-CH1,VL-CL]-human-IgG4-[hinge]-human-IgG4[N-terminal region of CH2]-human-IgG3*[C-terminal region of CH2:>aa position 251]-human-IgG3*[CH3]
rat-IgG2b/mouse-[VH-CH1,VL-CL]-human-IgG1-[hinge-CH2-CH3]
rat-IgG2b/mouse-[VH-CH1,VL-CL]-human-IgG2-[hinge-CH2-CH3]
rat-IgG2b/mouse-[VH-CH1,VL-CL]-human-IgG3-[hinge-CH2-CH3, oriental allotype]

rat-IgG2b/mouse-[VH-CH1,VL-CL]-human-IgG4-[hinge-CH2-CH3]
human-IgG1/human-[VH-CH1,VL-CL]-human-IgG1-[hinge]-human-IgG3*-[CH2-CH3]
human-IgG I/rat-[VH-CH1,VL-CL]-human-IgG1-[hinge]-human-IgG4[N-terminal region of CH2]-human-IgG3*[C-terminal region of CH2:>aa position 251]-human-IgG3*[CH3]
human-IgG1/mouse-[VH-CH1,VL-CL]-human-IgG1-[hinge]-human-IgG4[N-terminal region of CH2]-human-IgG3*[C-terminal region of CH2:>aa position 251]-human-IgG3*[CH3]
human-IgG1/rat-[VH-CH1,VL-CL]-human-IgG1-[hinge]-human-IgG2 [N-terminal region of CH2]-human-IgG3*[C-terminal region of CH2:>aa position 251]-human-IgG3*[CH3]
human-IgG1/mouse-[VH-CH1,VL-CL]-human-IgG1-[hinge]-human-IgG2 [N-terminal region of CH2]-human-IgG3*[C-terminal region of CH2:>aa position 251]-human-IgG3*[CH3]
human-IgG1/rat-[VH-CH1,VL-CL]-human-IgG1-[hinge]-human-IgG3*-[CH2-CH3]
human-IgG1/mouse-[VH-CH1,VL-CL]-human-IgG1-[hinge]-human-IgG3*-[CH2-CH3]
human-IgG2/human-[VH-CH1,VL-CL]-human-IgG2-[hinge]-human-IgG3*-[CH2-CH3]
human-IgG4/human-[VH-CH1,VL-CL]-human-IgG4-[hinge]-human-IgG3*-[CH2-CH3]
human-IgG4/human-[VH-CH1,VL-CL]-human-IgG4-[hinge]-human-IgG4[N-terminal region of CH2]-human-IgG3*[C-terminal region of CH2:>aa position 251]-human-IgG3*[CH3]
mouse-IgG2b/rat-[VH-CH1,VL-CL]-human-IgG1-[hinge]-human-IgG3*-[CH2-CH3]
mouse-IgG2b/human-[VH-CH1,VL-CL]-human-IgG1-[hinge]-human-IgG3*-[CH2-CH3]
mouse-IgG2b/mouse-[VH-CH1,VL-CL]-human-IgG1-[hinge]-human-IgG3*-[CH2-CH3]
mouse-[VH-CH1,VL-CL]-human-IgG4/rat-[VH-CH1,VL-CL]-human-IgG4-[hinge]-human-IgG4-[CH2]-human-IgG3*-[CH3]
human-IgG1/rat-[VH-CH1,VL-CL]-human-IgG I-[hinge]-human-IgG4-[CH2]-human-IgG3*-[CH3]
human-IgG1/mouse-[VH-CH1,VL-CL]-human-IgG1-[hinge]-human-IgG4-[CH2]-human-IgG3*-[CH3]
human-IgG4/human-[VH-CH1,VL-CL]-human-IgG4-[hinge]-human-IgG4-[CH2]-human-IgG3*-[CH3]

Preferably, the antibodies useful according to the present invention are monoclonal, chimeric, recombinant, synthetic, semi-synthetic, or chemically modified intact antibodies having for example Fv, Fab, scFv, or F(ab)$_2$ fragments.

Preferably, antibodies or derivatives or fragments thereof of human origin are used, or those modified to be suitable for the use in humans (so-called "humanized antibodies") (see for example Shalaby et al., J. Exp. Med. 175 (1992), 217; Mocikat et al., Transplantation 57 (1994), 405).

The preparation of the different types of antibodies and antibody fragments mentioned above is well-known to the skilled artisan. The preparation of monoclonal antibodies, preferably of mammalian origin, e.g., of human, rat, mouse, rabbit, or goat, can be performed using conventional methods as those described for example in Köhler und Milstein (Nature 256 (1975), 495), in Harlow and Lane (Antibodies, A Laboratory Manual (1988), Cold Spring Harbor) or in Galfré (Meth. Enzymol. 73 (1981), 3) or in DE 195 31 346.

It is further possible to prepare the antibodies described by means of recombinant DNA technology according to techniques known to the skilled artisan (see Kurucz et al., J. Immunol. 154 (1995), 4576; Hollinger et al., Proc. Natl. Acad. Sci. USA 90 (1993), 6444).

The preparation of antibodies having two different specificities, so-called bispecific antibodies, can be performed on the one hand using recombinant DNA technology but on the other hand also by the so-called hybrid hybridoma fusion technique (see for example Milstein et al., Nature 305 (1983), 537). This technique includes the fusion of hybridoma cell lines each producing antibodies with one of the desired specificities and identifying and isolating recombinant cell lines producing antibodies with both specificities.

The problem underlying the present invention is solved using the trifunctional bispecific antibodies as defined in claim 1. In the following, the preparation of antibodies showing two specificities is described in more detail. Trifunctional bispecific antibodies falling under the present invention belong to the prior art, and references describing such methods of preparation are incorporated herein by reference in their entirety.

Trifunctional bispecific antibodies are composed of two antibody semi-molecules (each having a H and a L immunoglobulin chain) each representing a specificity, and having an Fc portion like normal antibodies which performs the well-known effector functions. They are preferably prepared using the quadroma technology. This method of preparation is exemplified in DE-A-44 19 399. For complete disclosure this document is incorporated by reference in its entirety also with respect to a definition of bispecific antibodies. It should be understood that also other methods of preparation are useful if they lead to the trifunctional bispecific antibodies according to the above definition which are required according to the present invention.

The binding of the trAb to Fcγ-RI shows two essential advantages with regard to an optimal anti-tumor effectivity:
(1) Fcγ-RI-positive cells have the ability to eliminate tumor cells by ADCC and, thus, are able to contribute synergistically to the anti-tumor effect of the cytotoxic T cells directed to the tumor cell by the trAbs.
(2) FcγRI-positive cells (such as monocytes/macrophages/dendritic cells) are able to provide important co-stimulatory signals similar to antigen presentation to the T cell and, thereby, preventing T cell anergy. Furthermore, even T cells having a T cell receptor which recognizes tumor-specific peptides (presented via MHC antigens on the tumor cell) can be stimulated as a desired by-product due to the trAb-mediated interaction of the T cell with accessory cell and tumor cell. In this constellation, the co-stimuli necessary for correct activation of the T cell would be provided by the accessory cell (such as the monocyte). Thus, besides the direct T cell receptor-independent trAb-mediated tumor destruction the antibody of the present invention should also be able to activate and generate tumor-specific T cells which after degradation of the trAb continue to patrol in the patient. This means, that similar to gene-therapeutical approaches (e.g., by incorporation of co-stimulatory antigens such as B-7 into the tumor cell) the tumor tolerance in the patient may be abolished by trifunctional bispecific antibodies.

The following experimental data show that trAbs as described herein can be surprisingly highly efficiently used for the destruction of tumor cells with only a low to medium expression level of the target antigens, particularly preferred of Her2/neu and CD20 target antigens. The reason for the high efficiency is to be found in the mode of action of said trifunctional antibodies as described before. The mode of action is significantly different from monospecific antibodies. Trifunctional antibodies as used in the present invention are able to target and simultaneously activate different types of immune cells by their anti-T cell binding arm and their Fc-portion. Typical examples of these immune cells are T lymphocytes and accessory cells with Fcγ-receptor types I (CD64) and III (CD16). While the first binding arm binds to the target antigen on the tumor cell like Her2/neu or CD20, the second binding arm binds to e.g. CD3 on T lymphocytes (FIG. 4).

Methods on how to quantify the expression level of a tumor antigen are known in the art. E.g. immunocytochemical methods like e.g. ELISA tests, quantitative flow cytometry, tissue staining methods and cytospin analysis. A typical example for a quantitative determination method for the expression of tumor-associated target antigens on a tumor cell is an immunohistochemical method like the HERCEPTEST® developed by DAKO, Glostrup, Denmark allowing the quantitative determination of the expression level of Her2/neu on tumor tissues. Reference is made to the HERCEPTEST® as described by DAKO for the DAKO Cytomation Autostainer Code no. K5207, first edition, to be identified by the publication no. 111 781-001 and K5207/EFG/AOS/13.10.04 which is fully incorporated herein by reference. An evaluation system is provided for Her2/neu comprising four steps 0, 1+, 2+, 3+ referring to an approximate number of expressed target antigens on the surface of a tumor cell. In accordance with this system, cells with an expression of less than 20,000 Her2/neu molecules on the target cell surface are classified as negative; cells with an expression of more than about 20,000 and up to about 100,000-110,000 (up to a maximum of 150,000) molecules are classified as 1+ (low expression), cells with an expression of up to about 500,000 molecules as 2+ (medium expression), and cells with an expression of between about 2,000,000 to 10,000,000 molecules are classified as 3+ (high expression). In accordance with the present invention, it has been found that trifunctional bispecific antibodies directed against Her2/neu can be used for the treatment of patients having tumor cells classified as Her2/neu 1+ and 2+ (if the latter is additionally tested FISH negative) in accordance with the HERCEPTEST®.

The so-called FISH test is well known in the art. "FISH" means "Fluorescent In Situ Hybridization" and is a cytogenetic technique which can be used to detect and localize the presence or absence of specific DNA sequences on chromosomes. The method itself is well-established and known in the art. Reference is made for instance to Laudadio J, Quigley D I, Tubbs R, Wolff D J. HER2 testing: a review of detection methodologies and their clinical performance which is fully incorporated herein by reference.

A FISH negative test result means that the Her2/neu gene is not amplified; the number of Her2/neu genes is within the normal physiological range. However, in 15 to 20% of all mammary carcinomas, the Her2/neu gene is amplified. A detection of this amplification has been established to be crucial for the therapy of breast cancer. In cases where the Her2/neu gene is amplified, the FISH analysis will be positive and in those cases for instance a therapy with HERCEPTIN® might be successful. On the other hand, patients overexpressing Her2/neu but being FISH negative cannot be effectively treated with antibodies like HERCEPTIN®. Hence, it has to be considered as an important progress in the therapy of breast cancer that also patients with an expression of Her2/neu of up to 500,000 but being FISH negative can be successfully treated by the trifunctional bispecific antibodies as described herein. Various groups investigated also the expression of CD20 on B cell malignancies. Ginaldi et al., (J. Clin. Pathol., 51:364, 1998) assessed CD20 expression on different B cell malignancies by using the QUANTUM™ SIMPLY CELLULAR® microbeads kit (Sigma, St. Louis, Mo., USA). They found e.g. for B-CLL mean values of 65,000 CD20 molecules/leukemic cell and 123,000 CD20 molecules/cell for mantel cell lymphoma. In the case of hairy cell leukemia this investigation determined a mean value of 312,000 CD20 molecules/cell.

Huh et al., (Am J Clin Pathol 116:437, 2001) further investigated the different expression of CD20 at different sites as e.g. peripheral blood and bone marrow for B cell malignancies with a comparable method. Here, the number of CD20 molecules per cell is lowest in B-CLL (mean 4,067; range 222-46,395), higher in follicular lymphoma (mean 22,240; range 3,689-39,643), mantel cell lymphoma (mean 29,770; range 2,785-97,727) and highest in hairy cell leukemia (mean 31,563; range 1,607-72,540) in bone marrow specimens. In contrast, in peripheral blood the number of CD20 molecules/cell was generally higher for e.g. B-CLL where the mean number was 9,051 ranging from 563-31,507.

Taken together, in the case of B cell malignances the number of CD20 molecules/cell varied from about 1000 up to 300,000 dependent on the type of B cell malignancy and the site in the body and up to a maximum of about 350,000.

In the following examples and with reference to the enclosed figures and tables, the invention is described in more detail. The first example illustrates the present invention with respect to the trifunctional antibody available under the trademark REXOMUN® (INN-name, ertumaxomab) and the tumor-associated antigen Her2/neu targeted by REXOMUN®. The second example is directed to a trifunctional bispecific antibody named Bi20 (also known as FBTA05) that binds to a T cell via CD3 and recognizes CD20 as tumor antigen. These examples provide convincing evidence that the invention can be used with respect to all other tumor-associated antigens as specified in claim 1 and throughout the specification. All these tumor-associated antigens may be present on the surface of the tumor cell in such a low number so that they can hardly be treated by conventionally used antibody-based immune therapy.

The figures and tables of the present description are explained as follows in connection with examples 1 and 2.

FIG. 1: A-F Her2/neu expressing profiles of cell lines Lox, HCT-8 and SKBR3 with different anti Her2 antibodies measured by flow cytometry.

FIG. 2a: Killing of Her2+3 SKBR-3 cells: Dot plot analysis with the Micrometastasis Detection System; * number corresponding to table 3

FIG. 2b: Killing of Her2+1 HCT-8 cells: Dot plot analysis with the Micrometastasis Detection System; * numbers corresponding to table 3

FIG. 2c: Killing of negative Her2 Lox cells: Dot plot analysis with the Micrometastasis Detection System; * numbers corresponding to Table 3

FIG. 2d: Killing of Her2+1 HCT-8 cells; Dot plot results of donor 2 as an example for the MDS workflow; * numbers corresponding to table 3

FIG. 3: Cytokine secretion in clonogenic assay supernatants after 24 h measured with the Cytokine Bead Array system (CBA)

FIG. 4: The postulated tri-cell-complex. The trifunctional antibody is able to accelerate the recognition and destruction of tumor cells by different immunological mechanisms. Bei der Auflistung der Zytokine im Bild sollte man noch IFN-γ aufnehmen Note: ADCC, Antibody dependent cellular cytotoxicity; DC, Dendritic cell; NK, Natural killer cell; DC-CK1, Dendritic cell cytokine 1; IL, Interleukin; LFA, Leukocyte function associated antigen; TNF-α, Tumor necrosis factor α; CD, Cluster of differentiation (adapted from Ruf & Lindhofer, 2001)

Figure 5B:
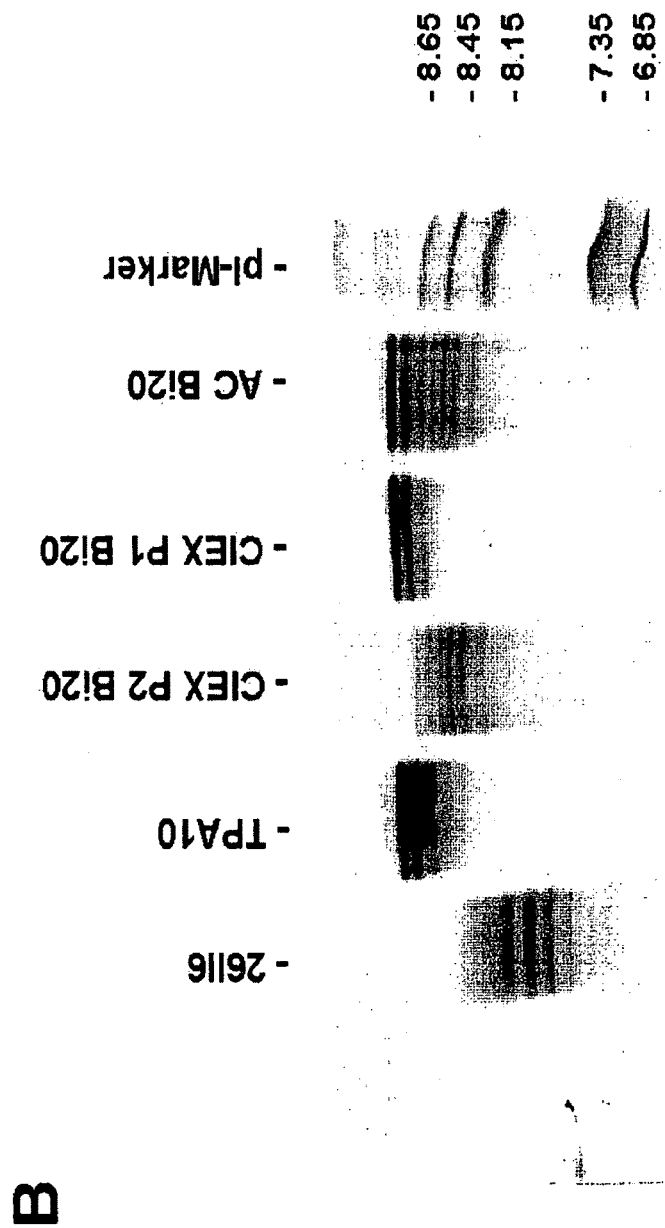

FIG. 5. Purification of Bi20. (A) Cationic exchange chromatography (CIEX). Parental mouse antibodies (Peak 1) were separated from trifunctional antibodies (Peak 2) on a HR10/10 high performance SP-SEPHAROSE® column. (B) Isoelectric focusing (IEF) of Bi20 trifunctional antibody purification. Parental rat antibodies (26II6) were removed after protein A affinity chromatography (AC Bi20), and parental mouse antibodies (TPA10) were separated from trifunctional antibodies by CIEX (CIEX P1 Bi20). Purified Bi20 was found in Peak 2 of the cationic exchange chromatography (CIEX P2 Bi20).

FIG. 6. Bi20 specifically binds to effector cells. 190 ng Bi20 was incubated with $5 \times 10^5$ target cells, and binding was measured by FACS analysis. Ramos cells (A) were used as target cells for the CD20 arm, and THP-1 cells (B) were used for the Fc part. For competition assays, cells were pre-incubated with Rituximab (Rit) at the indicated excess of antibody for 30 minutes.

Figure 7A:
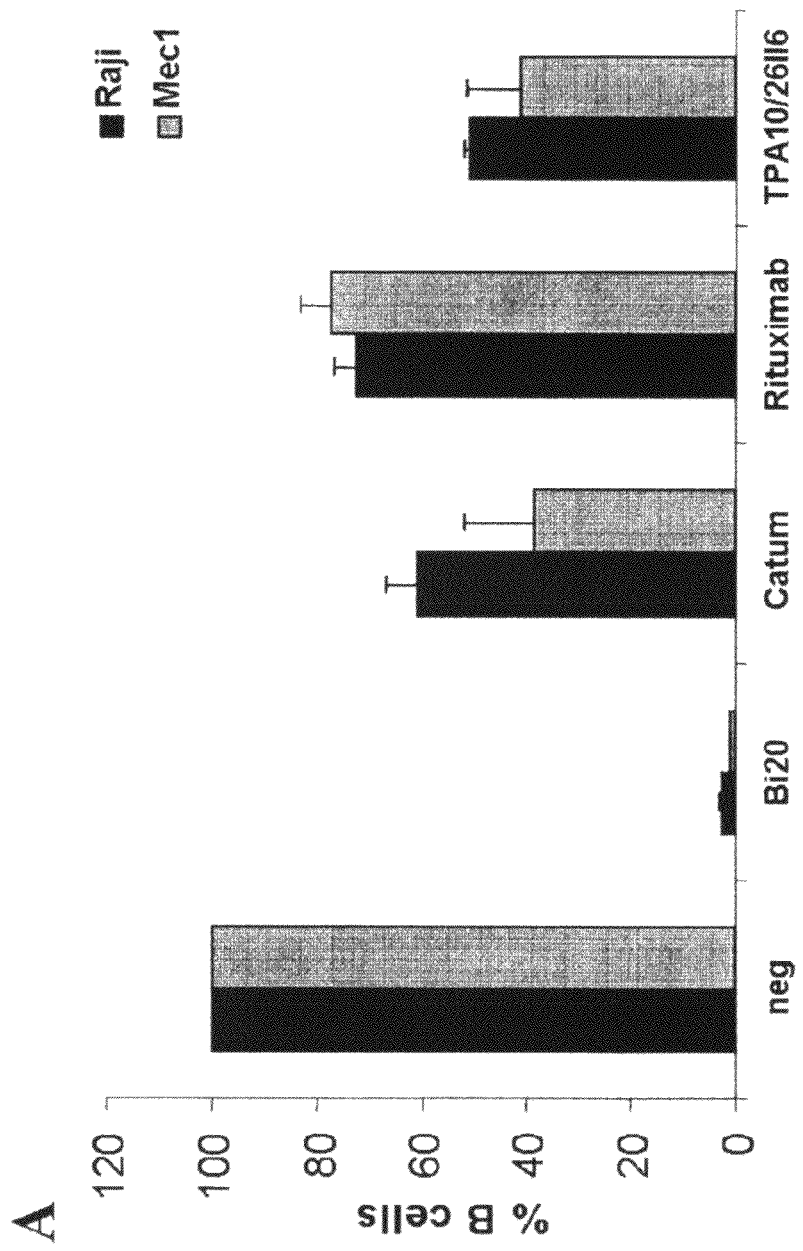
Figure 7B:
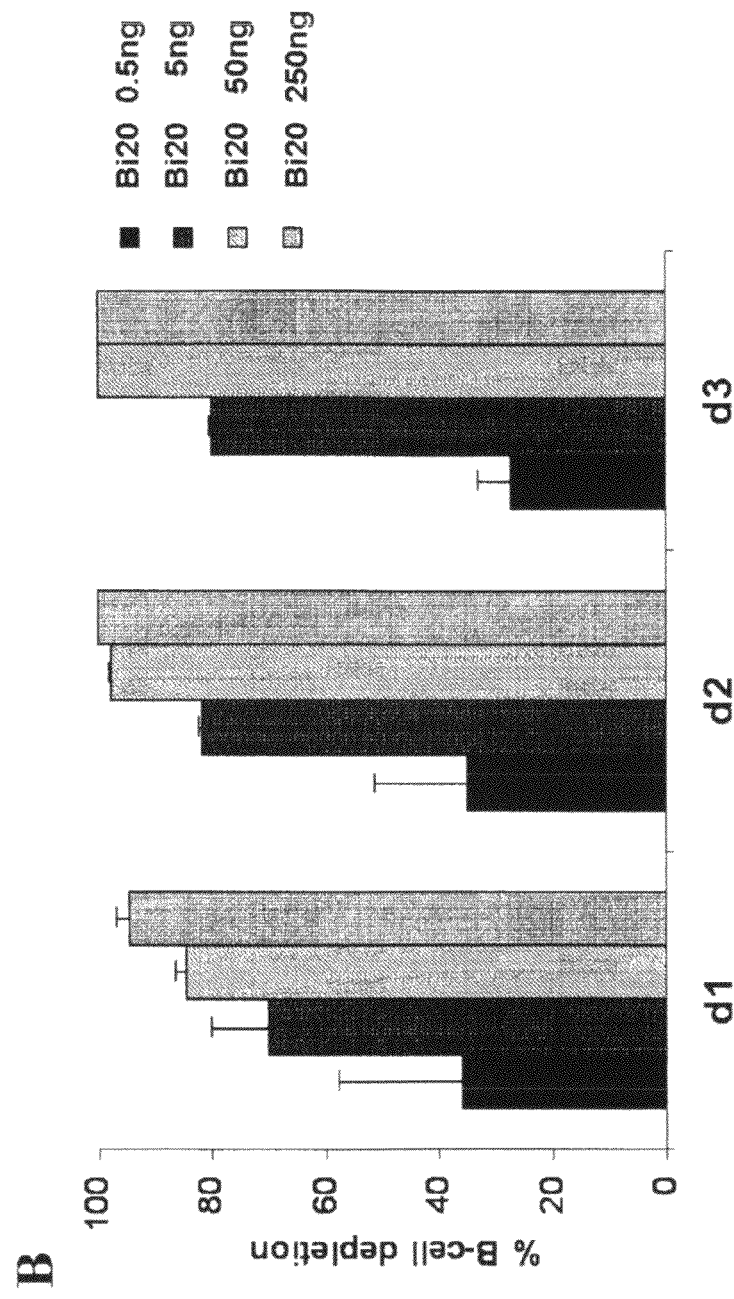

FIG. 7. Bi20 mediates efficient B-cell depletion in the presence of effector cells. (A) 1×10⁶/ml PBMCs and 2×10⁵/ml tumor cells (Raji, Mec1) were incubated with 50 ng/ml of Bi20, catumaxomab (Catum), rituximab, or parental antibodies TPA10 and 26II6. B-cell elimination was determined on day 3 by trypan blue exclusion counting and FACS analysis of monocytes, B cells, and T cells. The absolute B cell number in the assays without antibody (neg) was set as 100%. (B) 1×10⁶/ml PBMCs and 2×10⁵/ml Raji cells were incubated with increasing amounts (0.5-250 ng/ml) of Bi20. The absolute B cell count was determined on days 1, 2, and 3 by trypan blue exclusion and FACS analysis, and the percentage of B cell depletion was calculated.

FIG. 8. Bi20 mediates activation of T cells. (A) 1×10⁶/ml PBMCs and 2×10⁵/ml Raji tumor cells were incubated with 50 ng/ml of Bi20, catumaxomab (Catum), rituximab, or parental antibodies TPA10 and 26II6 for 3 days. MFI of CD25 expression on $CD4^+$ and $CD8^+$ cells was determined by FACS analysis. (B) PBMC and Raji cells were incubated with increasing amounts (0.5-250 ng/ml) of Bi20. MFI of CD25 expression on $CD4^+$ T cells was measured on days 1, 2, and 3.

Figure 9:
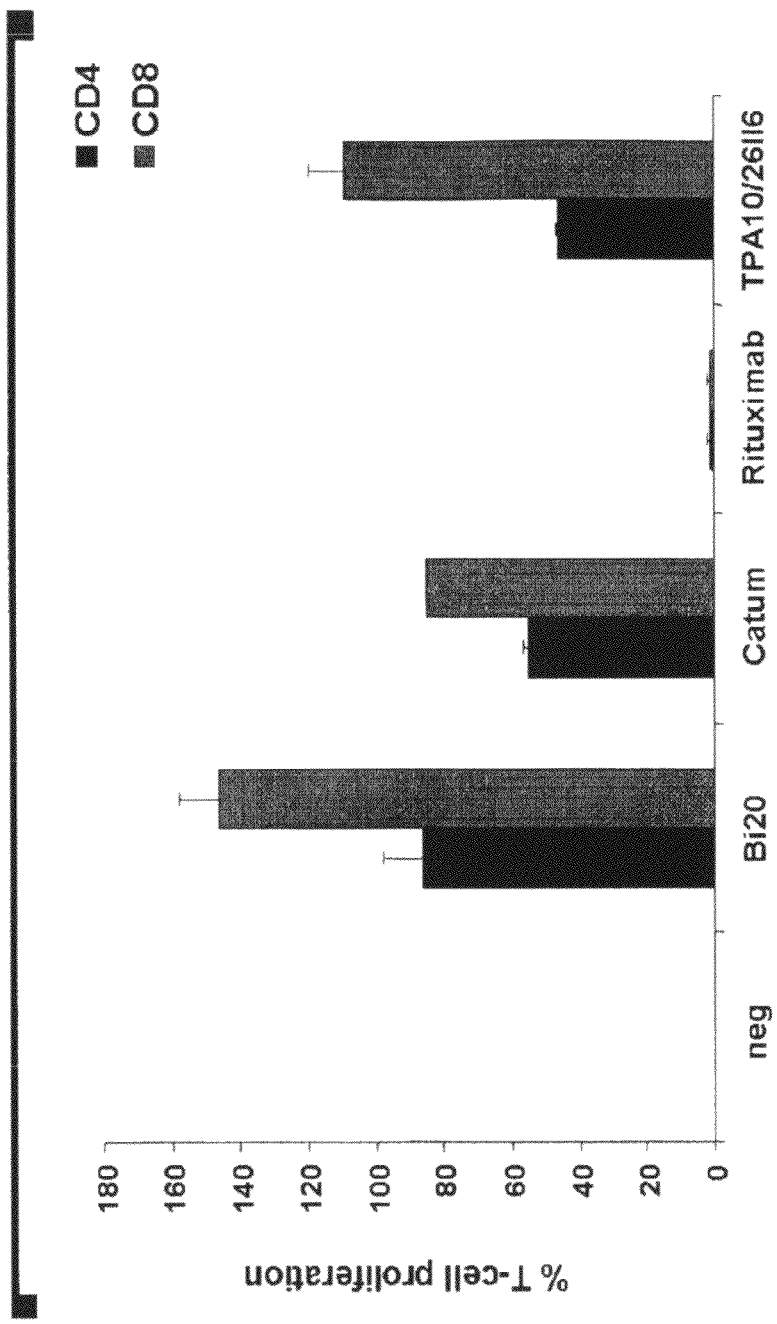

FIG. 9. Bi20 induces proliferation of T cells. 1×10⁶/ml PBMCs and 2×10⁵/ml Raji cells were incubated with Bi20, catumaxomab (Catum), rituximab, or parental antibodies TPA10 and 26II6 at a concentration of 50 ng/ml for 3 days. T cell number was determined by trypan blue exclusion counting and FACS analysis with anti-CD5/4 and anti-CD5/8 antibodies.

FIG. 10. Bi20-mediated activation of monocytes. (A) 1×10⁶/ml PBMCs and 2×10⁵/ml Raji tumor cells were incubated with 50 ng/ml of Bi20, catumaxomab (Catum), or rituximab for 1 day. MFI of CD25 expression by $CD14^+$ monocytes was determined by FACS analysis. (B) 1×10⁶/ml PBMCs and 1×10⁵/ml THP-1 cells were incubated with 50 ng/ml of Bi20, catumaxomab (Catum), rituximab (Rit), TPA10, or 26II6 for 1 day. Activation of $CD33^+$ THP-1 cells was determined via CD25 or CD40 expression.

FIG. 11. Bi20 induces depletion of CLL B cells in the presence of healthy donor effector cells. (A) 1×10⁶/ml PBMCs and 2×10⁵/ml CLL tumor cells were incubated with 5, 50, or 250 ng/ml Bi20, 250 ng/ml catumaxomab (Catum), or 250 ng/ml Rituximab (Rit) for 3 days. B cell elimination was determined on day 3 by trypan blue exclusion counting and FACS analysis of monocytes, B cells, and T cells. The absolute B cell number in the assays without antibody (neg) was set as 100%. MV: mean value of CLL-1 to CLL-9. (B) Overview of CD20 expression in CLL patient samples (1-14), cell lines (Raji, Mec-1), and one healthy donor (PBMC). MFI=mean fluorescence intensity.

Table 1: Characteristics of used antibodies and their corresponding detection antibodies
   * TRION Pharma, Munich, $ Roche, # Micromet, Munich Table 2: Used cell lines and their Her2/neu score
   *: according to Ross et al., Molecular and Cellular Proteomics 3:379-398, 2004

Table 3: Clonogenic assay samples
   Ab=Antibody, µg=micrograms, ng=nanograms

Table 4. Bi20 mediates cytokine secretion. 1×10⁶/ml PBMCs and 2×10⁵/ml tumor cells (Raji, Ramos, Mec1, Granta, DOHH-2) were incubated with 50 ng/ml Bi20, catumaxomab (Catum), rituximab, or parental antibodies TPA10 and 26II6 for 3 days. Supernatants were harvested, and cytokine secretion was measured with a CBA assay and FACS analysis.

Table 5. Bi20 mediates elimination of CLL B cells in vitro in an autologous setting. Percentages of B and T cells, CD20 expression (MFI) on B cells, and E:T ratio were determined immediately after CLL PBMC preparation and before incubation. CLL cells were incubated with the indicated amounts of Bi20 or rituximab on days 0, 3, 6, and 9. B cell elimination was determined as shown between day 3 and 10 depending on the patient sample. B cell elimination is indicated as % B cells depleted. T cell activation: CD25 expression on $CD4^+$ and $CD8^+$ T cells is at least five-fold (++) up-regulated. Effector/target ratio (E:T) was defined as the number of monocytes, NK cells, and T cells versus the number of B cells. B cell elimination ≤10% was rated as negative (neg).

EXAMPLE 1

Example 1 is directed to the characterization of a Her2/neu binding trifunctional bispecific antibody with respect to its ability to be used for the treatment of patients with the score 1+ in the HERCEPTEST®.

Methods

Cell Lines and Antibodies

REXOMUN® (produced by Trion Pharma, Munich) is a trifunctional antibody which targets with one binding arm the tumor-associated antigen Her2/neu and binds with the other arm the CD3 molecule on T cells. Furthermore REXOMUN® binds FcγRI and FcγRIII positive cells (e.g., macrophages, NK cells, dendritic cells) with its potent Fc region consisting of mouse IgG2a and rat IgG2b isotypes. Monoclonal antibody 2502A (Trion Pharma, Munich) is specific for Her2/neu and is one of the parental antibodies which are included in REXOMUN®. 26II6 (Trion Pharma, Munich) is specific for CD3 and is the other parental antibody which is included in REXOMUN®. 520C9 (ATCC HB-8696) is another monoclonal antibody recognizing the Her2/neu receptor. Trastuzumab is a humanized anti-Her2 monoclonal antibody developed from the murine anti-Her2/neu antibody Mab 4D5.[58] Table 1 shows the characteristics of the used antibodies and their corresponding detection antibodies.

SKBR3 (ATCC H TB-30) is a breast cancer cell line with a strong overexpression of Her2/neu (HERCEPTEST® score+3) detected by IHC.[58] HCT-8 (ATCC CCL-244) is a colon carcinoma cell line and Lox is a melanoma cell line (table 2).

Her2/Neu Scoring

Her2/neu status of HCT-8 cells was assessed by IHC using the HERCEPTEST® kit (DAKO, Glostrup, Denmark) and was performed by the Institute of Pathology, LMU Munich according to the manufacturer's manual.

FACS Analysis

FACS analysis was performed with 5×10⁵ target cells (SKBR3, HCT-8 or Lox). Cells were incubated with 100 ng monoclonal antibodies or 100 ng of the trifunctional antibody REXOMUN® for 45 min at 4° C. Samples were then washed with phosphate buffered saline (PBS) without $Mg^{2+}$ and $Ca^{2+}$ (PAN Biotec, Aidenbach) and incubated with the corresponding detection antibodies (Dianova, Hamburg) (Table 1) for 45 min at 4° C. After another washing step with PBS, cells were resuspended in PBS containing 0.01 µg/ml ethidium bromide (Sigma, Munich). Amount of the antibody binding was analysed by mean fluorescence intensity in an overlay histogram. A sample with the anti-human detection antibody alone or a sample incubated with 26II6 (anti CD3) and its corresponding detection antibody (isotype control) served as negative controls. All FACS analysis was carried out on a FACSCALIBUR™ (Becton Dickinson, Heidelberg) and was analysed with CELLQUEST™ Pro or WinMDI 2.8.

Clonogenic Assay

Antibody-mediated tumor elimination was investigated with a long-term clonogenic assay with unstimulated effector cells. Therefore, 10⁶ PBMC were spiked with 5% target cells (SKBR3, HCT-8 or Lox) and seeded in 24 well plates (Greiner). Antibodies were added in different concentrations and combinations which are shown in Table 3. Samples of target cells alone and samples consisting of a mixture of target and effector cells without addition of any antibodies served as controls. Samples were incubated at 37° C./5% $CO_2$ and were fed every 3 days with RPMI 1640, L-Glutamine and 10% FCS. After 8 days of incubation, cells were harvested from the 24 well plates, washed with PBS w/o $Mg^{2+}/Ca^{2+}$ and counted in a Neubauer Cell Chamber with dead cell exclusion via trypan blue. Living cells were then spinned down on cytospin slides (Menzel) with a concentration of $2.5 \times 10^5$ cells per slide. Cytospins samples were dried overnight, followed by immunocytochemistry. Experiments were repeated 3 times with PBMC from 3 different donors.

Immunocytochemistry

Unspecific binding properties on the cytospin slides were saturated with 10% human sera. SKBR3 and HCT-8 cells were stained with 1.5 µg/slide anti-cytokeratin 8, 18, 19 antibody (A45B-B3, mouse IgG1, Micromet, Munich), Lox cells were stained with 1.5 µg/slide anti EGFR antibody (mouse IgG2a, kindly provided by Dr. Htun, Munich). The anti-mouse IgG1 ALEXA FLUOR® 477 (FITC) antibody (Molecular probes, Eugene) for cytokeratin staining or the anti-mouse IgG2a ALEXA FLUOR® 477 (FITC) antibody (Molecular probes, Eugene) for EGFR staining were used at 1.5 µg/slide as detection antibodies. Cytospin slides were analysed in a Micrometastasis detection system (MDS™, Applied Imaging) with a computerized image analysis counting FITC-labelled cells.

Colon Carcinoma Cell Line HCT-8 Shows a +1 her2/Neu Expression

The level of Her2/neu expression was investigated on different cell lines, in order to find a cell line that has a +1 expression of Her2/neu.

Therefore, FACS analysis with the monoclonal Her2/neu antibodies 2502A, 520C9, Trastuzumab and the trifunctional antibody REXOMUN® was performed. The monoclonal anti CD3 antibody 26II6 served as mock control. FIGS. 1 A-F shows the binding profiles of the used antibodies on SKBR3, HCT-8 or Lox cells. As controls served flow cytometry samples with the different detection antibodies only (FIG. 1A), isotype control was 26II6 (anti-CD3) with its corresponding detection antibody (FIG. 1B).

The melanoma cell line Lox—as expected—showed no expression for the Her2/neu receptor (FIGS. 1 C-F), whereas SKBR3 cells were stained heavily against Her2/neu with the monoclonal antibodies 520C9 (FIG. 1C), 2502A (FIG. 1D) and Trastuzumab (FIG. 1E). REXOMUN® stained SKBR3 cells to a lower extent, probably because of its one arm binding nature (FIG. 1F). HCT-8 cells compared to SKBR3 cells have a significantly weaker expression of the Her2/neu receptor with all used Her2 antibodies (FIGS. 1 C-F), justifying further evaluation of these cells. Her2/neu expression of HCT-8 cells was in addition analysed with the DAKO HERCEPTEST®. The test was performed by the Institute of Pathology (TU Munich). The colon carcinoma cell line HCT-8 showed a +1 expression of Her2/neu in the performed DAKO test, confirming the results of the FACS analysis. Table 2 shows a summary of used cell lines, their Her2/neu scores and the methods applied for determination of Her2/neu expression.

REXOMUN® is Able to Kill her2/Neu+3 and her2/Neu+1 Cell Lines In Vitro

REXOMUN®'s ability to simultaneously recruit and activate different types of immune cells to the tumor site led to the hypothesis, that REXOMUN® might also be able to eliminate Her2/neu (1+) low expressing tumor cells.

Therefore, a long-term cytotoxicity assay (clonogenic assay) was established. PBMC of 3 healthy donors were co-incubated either with the Her2/neu+3 expressing cell line SKBR-3, the Her2/neu-negative Lox cell line or the Her2/neu+1 expressing HCT-8 cell line for 8 days. Different antibody concentrations of Trastuzumab (100 µg/ml-1 µg/ml) or REXOMUN® (100 ng/ml-1 ng/ml) were added as shown in Table 3. Tumor cell killing was evaluated after 8 days by harvesting the cells, transferring them on cytospin slides and staining the cells with anti-CK 8, 18, 19 antibody (SKBR-3 and HCT-8) or anti EGFR-antibody (Lox) and the corresponding ALEXA FLUOR® FITC antibodies. The stained cytospin slides were then evaluated by a computerized image analysis using the SLIDE SCAN program on the Micrometastasis Detection System (MDS™, Applied Imaging, UK).

In this study the trifunctional antibody REXOMUN® (anti Her2/neu×anti CD3) was compared to the humanized anti-Her2/neu monoclonal antibody Trastuzumab in its ability to inhibit tumor cell growth of a low Her2/neu expressing tumor cell line HCT-8 (HERCEPTEST® score: +1).

Her2/neu expression on the cell lines SKBR3 (+3 HERCEPTEST® score), HCT-8 (+1 HERCEPTEST® score) and Lox (Her2/neu negative) were measured by FACS analysis, whereas HCT-8 cells were also tested via HERCEPTEST®. FACS analysis with various antibodies against Her2/neu showed strong Her2 expression on SKBR3 cells, a weaker expression on HCT-8 cells and no Her2/neu expression on Lox cells. These results correspond with the +1 HERCEPTEST® score of the HCT-8 cells. Mean fluorescence values of the trifunctional antibody REXOMUN® were slightly lower than the values of the monoclonal antibodies because of the monovalent binding of REXOMUN® compared to the bivalent binding of the monoclonal antibodies (FIGS. 1 A-F).

To test the ability of REXOMUN® and Trastuzumab to inhibit growth of the low Her2/neu expressing cell line HCT-8, clonogenic assays were performed. After eight days of culture cells were harvested from the culture dishes, were spinned on cytospin slides and stained for tumor cells. All control samples (12,500 tumor cells/24 well plate) without added antibodies (FIG. 2a-c, sample A1, B1, C1) showed tumor cell growth for the cell lines SKBR3, HCT-8 and Lox after cytospin staining in the MDS™. The slide with 250,000 PBMC without spiked tumor cells or added antibodies showed—as expected—no tumor cells at all (FIG. 2a-c, sample A2, B2, C2). Tumor growth was also clearly visible in the allogeneic controls where PBMC were mixed either with 5% of SKBR3, HCT-8 or Lox cells without addition of any antibody (FIG. 2a-c, sample A3, B3, C3).

Tumor cell growth of the Her2+3 cell line SKBR-3 was inhibited as expected by addition of 100 µg, 50 g, 10 µg and 1 µg Trastuzumab (FIG. 2a, samples A4-A8). Furthermore, REXOMUN® was also able to inhibit tumor growth by addition of only 100 ng, 50 ng, 10 ng or 1 ng. As shown in samples A9-A12 (FIG. 2a) tumor cells growth was inhibited more efficient than with Trastuzumab.

Tumor cell growth of the Her2/neu negative cell line Lox was neither inhibited by addition of various amounts of Trastuzumab nor REXOMUN® indicating the specificity of the tumor cell elimination driven by the presence of the Her2/neu receptor (FIG. 2c, sample C4-C12).

Remarkably, the growth of the colon carcinoma cell line HCT-8 (Her2/neu score+1) was not inhibited by various amounts (100 µg-1 µg) of Trastuzumab (FIG. 2b, sample B4-B8) which corresponds to previous findings with the Her2/neu+1 mammary carcinoma cell line MCF-7.5 Since MCF-7cells (ATCC HTB-22) show growth inhibition to TNF-α these cells could not be used in the clonogenic assays, as REXOMUN® like the trifunctional antibody REMOVAB® (anti EpCAM×anti CD3) triggers TNF-α secretion, because of its activation properties.[59] REXOMUN® however, was able to destroy the +1 Her2/neu cell line HCT-8 in concentrations as low as 100 ng, 50 ng and 10 ng/well (FIG. 2b sample B9-B11). 1 ng of REXOMUN® did not succeed to inhibit tumor cell growth of HCT-8 cells (FIG. 2b, sample B12). FIG. 2d shows the original MDS™ data plots for clonogenic assays of donor 2 using HCT-8 cells as target.

In conclusion, REXOMUN® is a therapeutic option not only for mammary carcinoma patients having +3 or +2 overexpression/gene amplification, but also for patients with low Her2/neu expression levels.

EXAMPLE 2

Here we describe the production and functional characterization of Bi20, a new trifunctional bispecific antibody directed against human CD3 and human CD20, particularly its ability to be used in the treatment of patients expressing the tumor antigen CD20 at only low levels.

CD20 is a 35-kDa non-glycosylated phosphoprotein that has been proposed to act as a calcium channel, playing a role in B-cell differentiation.[24] However, its exact function is still unknown as CD20-deficient mice show normal B-cell development and are also phenotypically normal.[25] CD20 was chosen as a target for directed immunotherapy for several reasons: (i) it is expressed exclusively on normal and malignant B cells but not on hematological precursor cells or cells in other human tissues,[26] (ii) it is expressed on most B-cell lymphoma cells,[27] and (iii) it is not shed or secreted upon antibody binding.[28,29] Furthermore, the suitability of CD20 as a target for tumor therapy has been clinically validated by the successful use of Rituximab, especially in combination with conventional chemotherapy.

In our present investigations we analyzed the in vitro properties of Bi20 in detail, demonstrating that this trAb efficiently kills human B cell tumor cells as well as cells derived from CLL patients that express only low levels of CD20. No preactivation of effector cells was necessary for tumor cell elimination, which was accompanied by a typical Th1 cytokine pattern and strong activation of T cells and monocytes. As an important prerequisite for clinical application, Bi20 can be purified easily and produced in sufficient amounts. Therefore, this trAb might offer new treatment options for thus far incurable NHL and CLL patients.

Materials and Methods
Antibodies and Reagents

The mouse cell line TPA10 producing a CD20-specific monoclonal IgG2a antibody was fused with 26II6, a rat cell line, secreting a CD3-specific IgG2b antibody, resulting in the quadroma cell line TPBs05 producing Bi20 (FBTAO5). Catumaxomab (REMOVAB®) was used as a trifunctional control antibody, consisting of the 26II16-derived CD3-specific arm and an anti-EpCAM specificity. Rituximab (MABTHERA®), a chimeric anti-CD20 antibody, was obtained from Roche (Basel, Switzerland). The anti-CD20 antibody and corresponding isotype were obtained from Beckman Coulter Immunotech (Krefeld, Germany). All other antibodies used for FACS analysis were purchased from BD Biosciences (Heidelberg, Germany). Propidium iodide was obtained from Sigma Chemicals (Deisenhofen, Germany).

Cell Lines and PBMC Preparation

The CLL cell line Mec1 was kindly provided by Dr. Michael Hallek (GSF, Munich, Germany). The Burkitt's lymphoma (BL) cell line Ramos was obtained from ATCC (USA). The BL cell line Raji, the NHL cell lines DOHH-2 and Granta, and the AML cell line THP-1 were purchased from the DSMZ (Braunschweig, Germany). Cells were grown in RPMI-1640 media (PAN-Biotech, Aidenbach, Germany) supplemented with 10% heat-inactivated FCS, nonessential amino acids, sodium pyruvate, and L-glutamate (PAN-Biotech). Human peripheral blood mononuclear cells (PBMCs) were isolated from heparinized blood of healthy donors by density gradient centrifugation using PANCOLL (PAN-Biotech). Peripheral blood samples from CLL patients were obtained after informed consent. The diagnosis of CLL was based on standard clinical and laboratory criteria. After purification, CLL cells were either immediately used or cryoconserved for later use. CLL cells were cultivated in IMDM (PAN Biotech) supplemented with 10% FCS. For assays in the autologous setting, only freshly prepared CLL cells were used.

Generation and Purification of Bi20

Bi20 was produced using the quadroma technology.[30] Supernatants of quadroma cells were tested for trAb binding to target cells by FACS analysis. TrAb-producing cells were subcloned several times to increase antibody production stability, and a master cell bank was established. TrAbs were purified from the quadroma cell culture supernatant by protein A affinity and ion exchange chromatography as described[31] using an ÄKTA purifier 100 (Amersham Biosciences, Uppsala, Sweden).

Isoelectric Focusing

Antibody samples were spotted onto a pH 7-11 ISOGEL® Agarose IEF (Cambrex Bio Science, Rockland, USA) and separated for 75 min at 1500 V, 50 mA, and 25 W. Antibody isoforms were visualized by staining with Coomassie brilliant blue (Sigma-Aldrich Inc., Missouri, USA), and gels were scanned for analysis.

FACS Analysis

Binding of antibodies to target cells, activation of effector cells, relative CD20 expression and cell subtype composition were analyzed by flow cytometry using a FACSCALIBUR™ (BD Biosciences, Heidelberg, Germany) equipped with a 488-nm argon laser. Data were analyzed using CELLQUEST™ Software (BD Biosciences).

To analyze antibody binding, $5\times10^5$ cells (Ramos, Jurkat, or THP-1) were incubated with Bi20 at the indicated concentrations for 30 minutes at 4° C., washed with PBS supplemented with 2% heat-inactivated FCS, and incubated with a FITC-labeled mouse anti-rat IgG detection antibody (Ramos) or a FITC-labeled rat anti-mouse antibody (Jurkat, THP-1) for 30 minutes at 4° C.

To characterize the activation properties of Bi20, $1\times10^6$/ml PBMCs and $2\times10^5$/ml human tumor cells were incubated with the indicated concentrations of antibodies for 1, 2, and 3 days at 37° C. in RPMI medium. Cells were harvested, washed, and incubated for 30 minutes at 4° C. with FITC- or PE-labeled detection antibodies directed against CD25 and CD69. Cell subtype composition was determined by staining $3\times10^6$ PBMCs with the following anti-CD antibody mixtures (FITC/PE/APC): 14/19/5, 4/8/5, 4/8/25, 45/3/5, and 16/56/5.

B-Cell Depletion Assays

Bi20-mediated B-cell depletion was determined using a bioassay. PBMCs ($1\times10^6$/ml) obtained from healthy donors were supplemented with $2\times10^5$/ml of the indicated tumor cells (Raji, Ramos, Mec1, DOHH-2, or Granta) or CLL patient cells (effector-to-target ratio 5:1) and incubated in the presence of the different antibodies at the indicated concentrations in 1 ml total volume. At days 1, 2, and 3 cells were collected and washed, and the percentage of viable B cells was analyzed by FACS analysis using a PE-conjugated anti-CD19 detection antibody. The total number of viable cells was determined by trypan blue exclusion counting. To examine antibody-mediated B-cell depletion in autologous CLL samples, PBMCs isolated from CLL patients were plated at a density of $2\times10^6$ cells/ml, and antibodies were added at the indicated concentrations on days 0, 3, and 6. FACS measurement and trypan blue exclusion counting were performed at the indicated time points.

Measurement of Cytokines

Bi20-induced cytokine release was determined under the same conditions used for the B-cell depletion experiments. Tumor B cell lines and PBMCs from healthy donors were incubated with 50 ng/ml of the indicated antibodies. After 3 days the supernatants were collected. Cytokines were measured with the human Th1/Th2 cytometric bead array (CBA, BD Biosciences, Heidelberg, Germany), which allows simultaneous analysis of IFN-γ, TNF-α, IL-2, IL-4, IL-6, and IL-10. Data acquisition and analysis were performed according to the manufacturer's protocol.

Results
Generation and Purification of Bi20

The trAb Bi20 was produced in quadroma cells and captured by protein A affinity chromatography. Parental rat antibodies do not bind to protein A and thus are absent from the eluate. Then, impurities such as parental mouse antibodies were removed by cationic exchange chromatography (CIEX) (FIG. 5A). Mouse antibodies eluted at 148 mM NaCl (FIG. 5A, Peak 1), whereas trAbs eluted at 320 mM NaCl. Isoelectric focusing of purified trAbs showed a distinct banding pattern with a pI range of −8.65-8.15. TrAbs were found only in peak 2 of the CIEX separation. No contaminating parental antibodies were detected.

Binding Specificities of Bi20

Figure 6A:
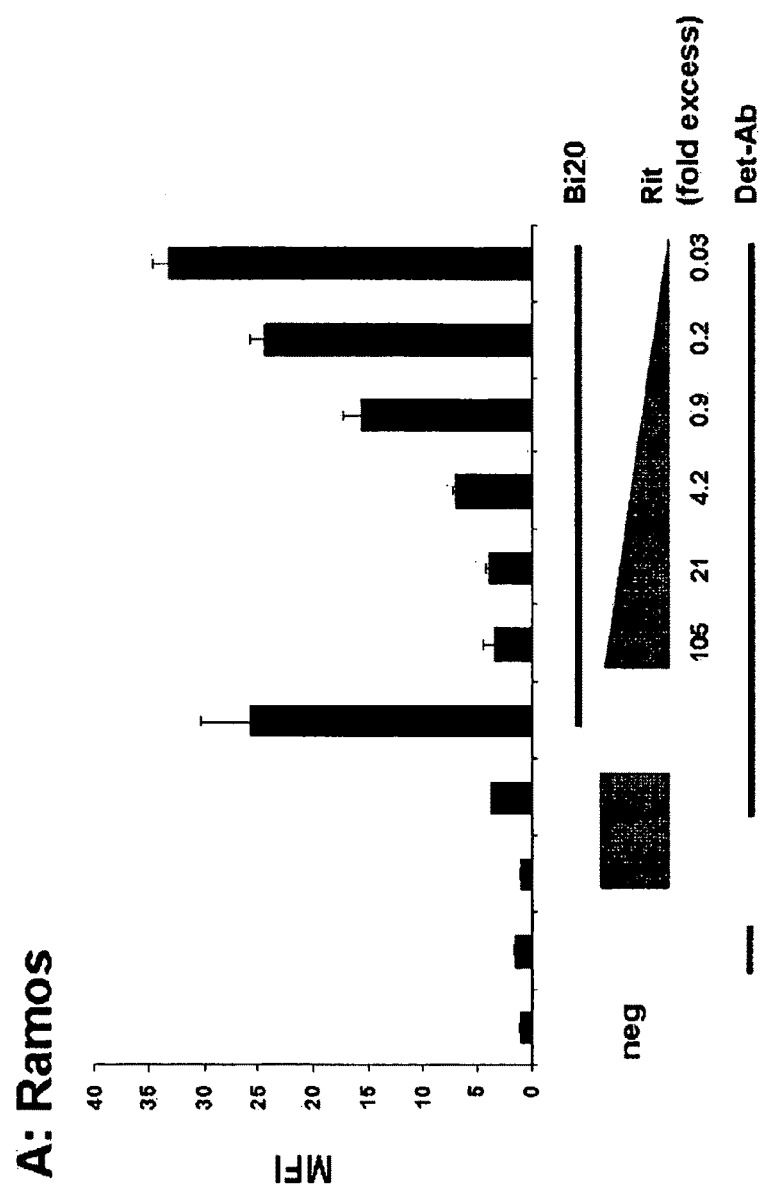
Figure 6B:
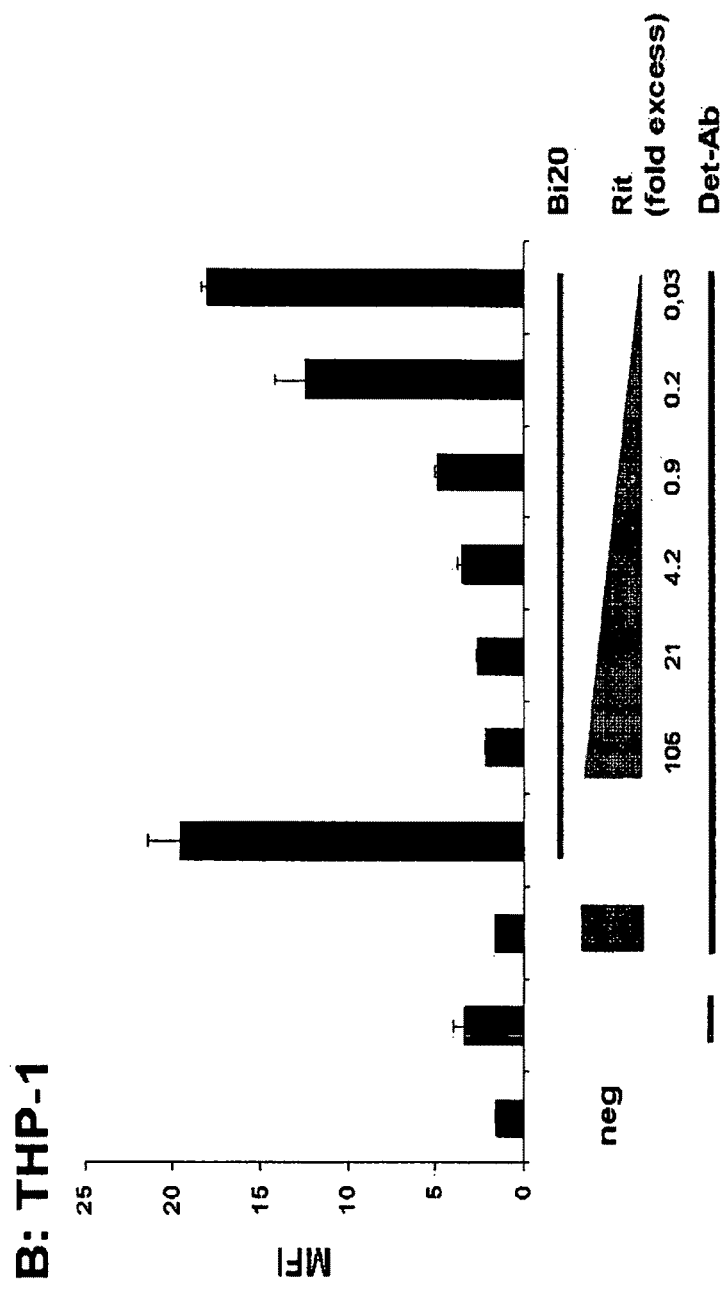

To demonstrate the trifunctional nature of Bi20, we examined its binding to specific target cells. We used the CD20 Burkitt's lymphoma cell line Ramos to confirm the functionality of the CD20-binding arm, the CD3 T-cell line Jurkat for the CD3-binding arm, and the monocyte cell line THP-1 to verify Fcγ-RI binding (FIG. 6). To confirm binding of Bi20 to CD20, competitive binding assays with Rituximab were performed. Bi20 binding on Ramos cells could be completely blocked by pre-incubation of the cells with a 21-fold excess of Rituximab (FIG. 6A). Similarly, binding of Bi20 to THP-1 cells could be competed away by Rituximab (FIG. 6B). Binding of Bi20 to CD3 on Jurkat cells was comparable to Bi20 binding to CD20 on Ramos cells (data not shown). Because the CD3-binding arm of Bi20 is identical to the corresponding arms in the well-characterized trAbs catumaxomab and ertumaxomab, no further analysis of the specificity of the CD3-binding arm was performed. In summary, these data confirm the trivalent binding mode of Bi20 and the specificity of binding.

Bi20 Mediates B-Cell Elimination

To study the effects of Bi20 on B-cell killing, we developed a FACS-based bioassay. Freshly prepared PBMCs without any pre- or costimulation were mixed with tumor B-cells at a ratio of 5:1 and 50 ng/ml of the indicated antibodies and incubated for 3 days. Cells were collected, and the composition of the subpopulations was determined by FACS analysis. Trypan blue exclusion counting was performed to obtain absolute cell numbers.

Using the CD20+ Burkitt's lymphoma cell line Raji as the target cell, effective B-cell elimination was observed with 50 ng/ml Bi20 (FIG. 7). As controls, we used the trAb catumaxomab (anti-EpCAM×anti-CD3), which does not bind to B cells (data not shown), and the parental antibodies 26II6 (anti-CD3) and TPA10 (anti-CD20). Catumaxomab (Catum) and the combination of the parental antibodies induced some B cell depletion, probably due to the release of cytokines such as IFN-γ and TNF-α (Table 4), indicating that the antitumor activity of Bi20 is indeed caused by its trifunctional design. Under these experimental conditions (low antibody concentration and E:T ratio), Rituximab mediated only a minor reduction in B cell numbers. Comparable data were obtained with the CLL cell line Mec1, which has 2.5-times lower CD20 expression than Raji cells (MFI 179 versus 428, data not shown).

These results encouraged us to analyze Bi20-mediated B cell depletion in more detail. Time-kinetic analyses showed depletion of Raji cells after only 24 h (FIG. 7B), when at least 35% of the B cells were eliminated at antibody concentrations as low as 0.5 ng/ml. At Bi20 concentrations of 250 ng/ml and 50 ng/ml, complete B cell depletion was observed on day 2 and day 3, respectively. Comparable results were found with Mec 1 cells (data not shown). Furthermore, we investigated whether B cell lines representing other lymphoma entities could be effectively killed. Efficient B cell depletion was detected when DOHH-2 (follicular lymphoma), Granta (mantle cell lymphoma), or Ramos (Burkitt's lymphoma) were used as target cells (data not shown).

Bi20 Mediates Activation of T Cells Independent of Concurrent B-Cell Binding

Figure 8A:
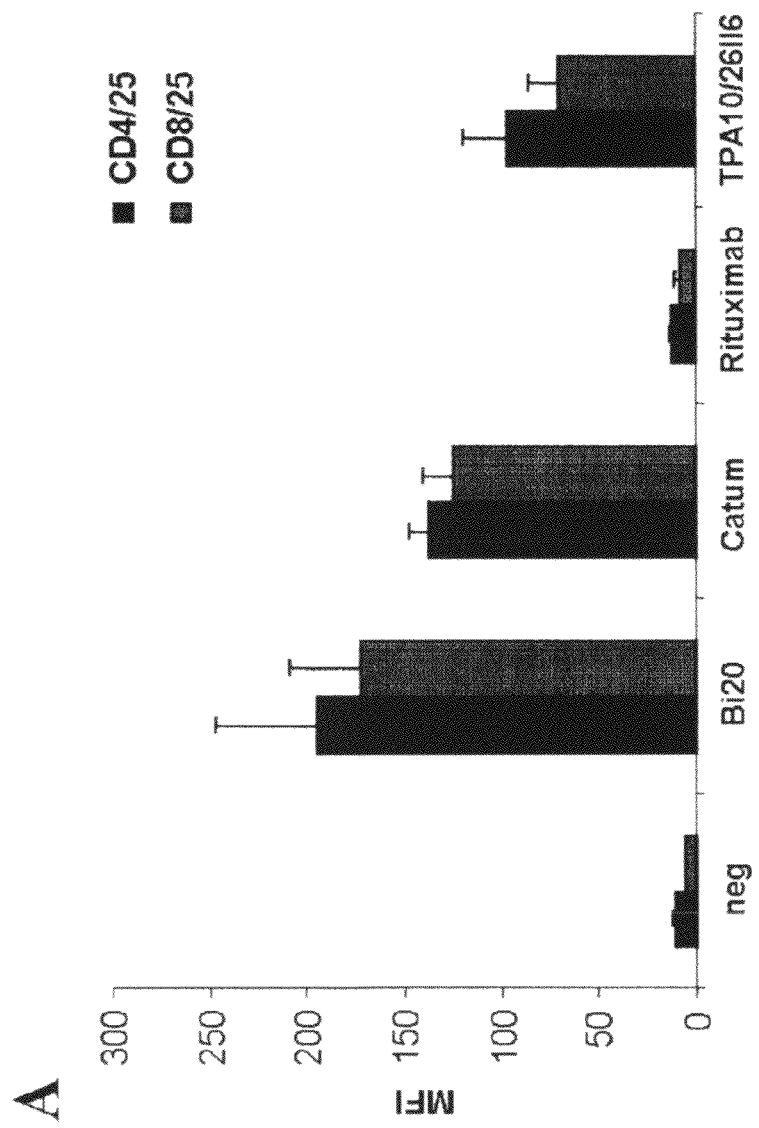

In contrast to previously described bispecific anti-lymphoma antibodies that display B cell cytotoxicity only after pre-stimulation with, e.g., anti-CD28 antibodies,[32] no pre-activation of T cells or monocytes was necessary for efficient B cell lysis induced by Bi20. Therefore, we asked whether effector cells could be activated upon Bi20 binding. PBMCs and Raji cells were incubated with the indicated antibodies, and up-regulation of the activation marker CD25 on CD4+ and CD8+ T cells was measured by flow cytometry (FIG. 8A).

Both Bi20 and catumaxomab induced a significant up-regulation of CD25 on CD4+ and CD8+ T cells, indicating that the simultaneous binding of the trAb to CD3 and CD20 is not necessary for T-cell activation. Up-regulation of CD25 was also observed with a combination of the parental antibodies 26II6 (anti-CD3) and TPA10 (anti-CD20). As expected, Rituximab did not induce any T-cell activation (FIG. 8A).

Figure 8B:
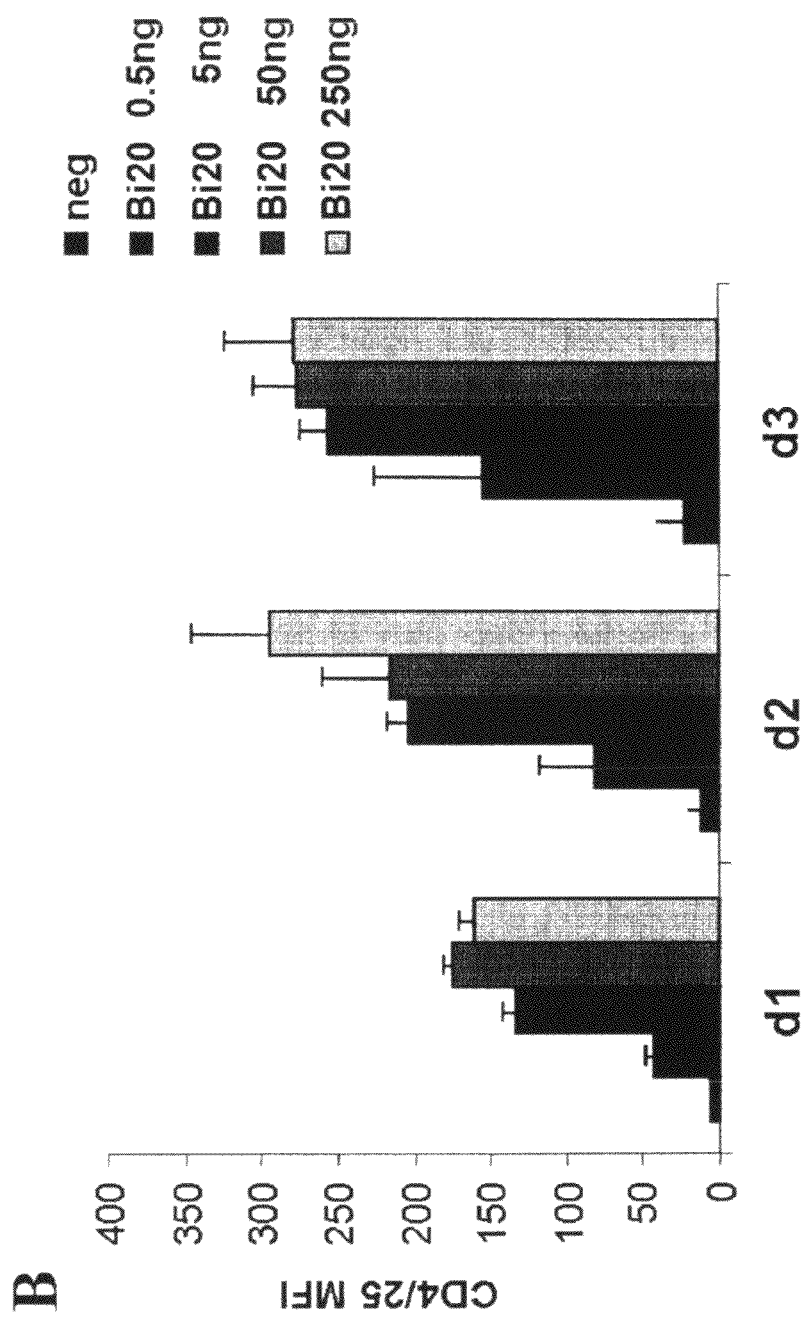

As shown in FIG. 8B, T cell activation depended on incubation time and antibody concentration, with maximal CD25 expression observed at day 2 for the highest Bi20 concentration (250 ng/ml). Other activation markers such as CD69 were also up-regulated, although to a lower extent and for a shorter time period (data not shown).

Bi20 Induces T-Cell Proliferation

In addition to T cell activation, we determined the increases in CD4+ and CD8+ T cell numbers induced by the different antibodies (FIG. 9). Incubation with Bi20 resulted in the preferential proliferation of T cells of the CD8+ subset compared to the CD4+ subset (145% versus 85% expansion of T cells), changing the CD4+:CD8+ ratio from 1.8:1 to 1.3:1. Catumaxomab and the parental antibodies also induced T-cell proliferation but to a lower extent than Bi20. As expected, Rituximab did not stimulate T cell proliferation. Notably, no stimulating agent other than the antibodies was necessary to induce proliferation.

Monocyte Activation is Dependent on Concurrent T Cell Binding but Independent of Simultaneous B Cell Binding Next, we addressed the question of whether Fcγ-RI/III+ cells such as monocytes/macrophages could also be activated by Bi20. PBMCs and Raji cells were incubated in the presence of different antibodies, and the activation of CD14+ cells was measured. As illustrated in FIG. 6A, both trAbs Bi20 and catumaxomab induced up-regulation of CD25 on CD14+ monocytes/macrophages, indicating that simultaneous B cell binding is not necessary for monocyte activation. In contrast, Rituximab, which binds B cells and monocytes/macrophages but not T cells via its Fc region, did not induce activation of CD14+ accessory cells. From these results we concluded that T-cell engagement is necessary for activation of accessory cells.

Figure 10A:
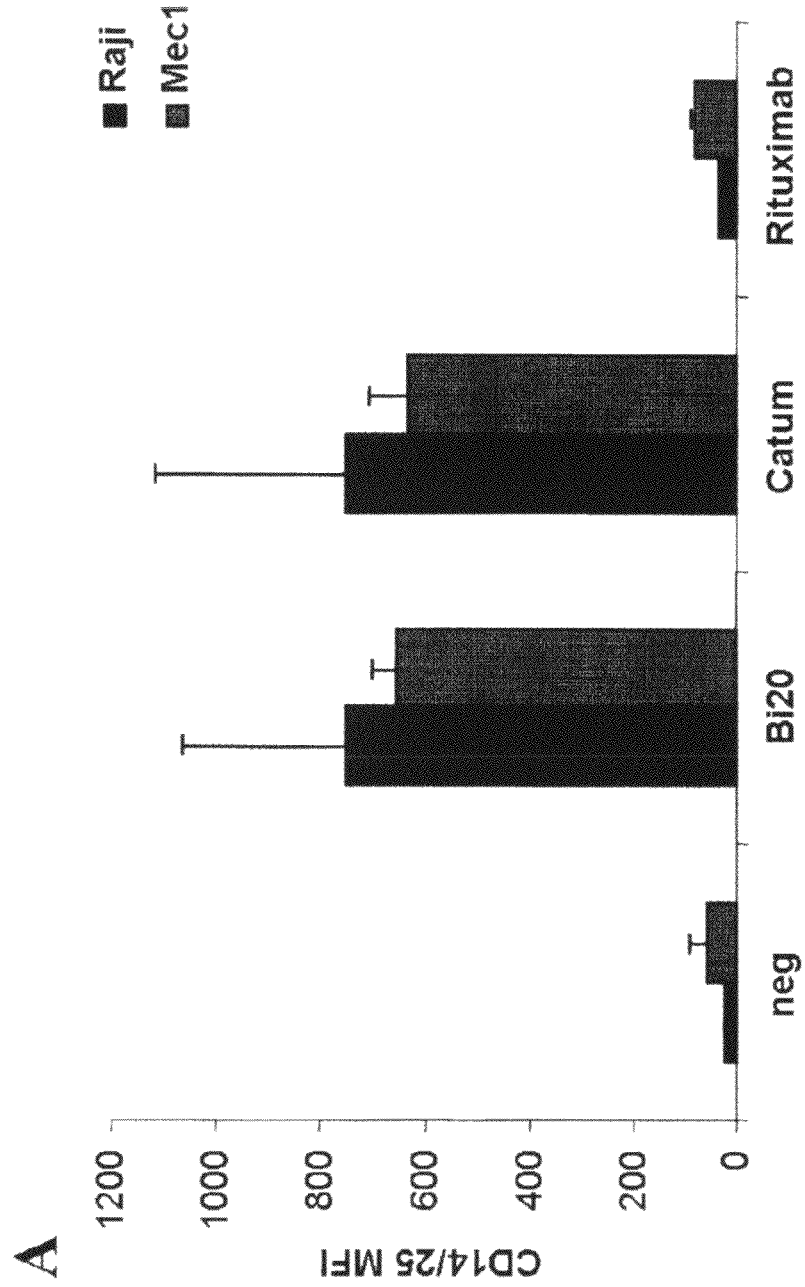
Figure 10B:
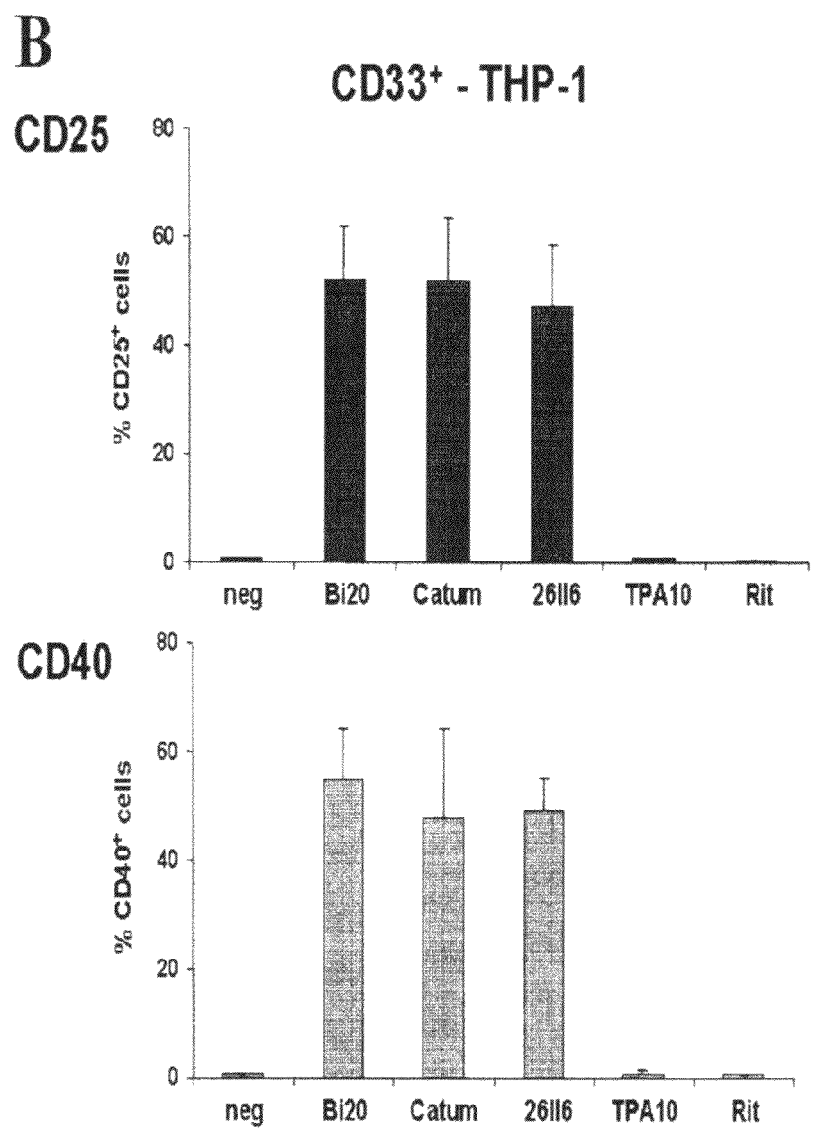

We confirmed this result using a slightly different system in the absence of malignant B cells. PBMCs and THP-1 cells were incubated in the presence of different antibodies, and the activation of CD33+ THP-1 cells was monitored via CD25 and CD40 expression (FIG. 10B). All antibodies that simultaneously bind THP-1 cells and T cells (Bi20, TPBs01, 26II6) activated THP-1 cells. In contrast, no activation was observed when antibodies were used that bind THP-1 and B cells but not T cells (TPA10, Rituximab). THP-1 cells in the absence of PBMCs were not activated by any of the antibodies (data not shown), indicating that concurrent binding of T cells and monocytes is an absolute prerequisite for monocyte activation in our experimental setting.

Bi20 Induces a Th1-Like Cytokine Profile

Since cytokine release is one of the immunological reactions that occurs after the therapeutic use of monoclonal antibodies,[33] we studied the cytokine profile induced by Bi20. PBMCs were incubated with different tumor cells (Raji, Ramos, DOHH-2, Granta, or Mec 1) and 50 ng/ml of antibodies. After 3 days, supernatants were collected and analyzed for the amounts of IFN-γ, TNF-α, IL-2, IL-4, 11-6, and IL-10 (Table 4).

Bi20 induced high levels of IL-6, which also was detected after incubation with the other antibodies at significantly lower levels. TNF-α was detected after Bi20 or catumaxomab treatment but not after incubation with Rituximab or the parental antibodies. A strong increase in IL-2 expression could be detected only after incubation with Bi20, confirming earlier investigations with trAbs showing that IL-2 was released only when all three binding partners (tumor cells, T cells, and accessory cells) are present.[18] IL-4, a marker of the Th2 lineage, was only marginally secreted, whereas IFN-γ, a Th1-specific cytokine, was strongly produced. Interestingly, IL-10, which can act as an inhibitory cytokine, was also released, suggesting an immunological counter-reaction. Similar results were obtained with all cell lines (Raji, Ramos, Mec1, DOHH-2, Granta; Table 4).

Bi20 Mediates Elimination of B Cells Derived from CLL Patients

We next investigated whether Bi20-mediated B cell depletion could be confirmed by using cells derived from CLL patients. Cells from nine different donors were incubated with PBMCs from healthy donors and Bi20 (5, 50, or 250 ng/ml) or control antibodies as illustrated in FIG. 11. Increasing concentrations of Bi20 led to improved elimination (up to 99%) of CLL B cells. Rituximab also induced significant B cell depletion, but even at a concentration of 250 ng/ml, nearly half of the B cells were viable. This shows that, at least in our experimental setting, the trAb Bi20 is much more potent than Rituximab with respect to the elimination of primary tumor cells from CLL patients. In this case, unspecific B cell depletion mediated by catumaxomab was substantially decreased compared to the previous experiments with B cell lines (FIGS. 7 and 11).

Remarkably, even when CLL B cells expressing very low levels of CD20 were tested (CLL 2, 3, and 4; FIGS. 1A and B), nearly all B cells were eliminated by Bi20 (99%, 93%, and 98%, respectively). In contrast, Rituximab showed less or no efficacy using cells from the same patient group (76%, 79%, and 1%, respectively).

Next, we addressed the crucial question of whether Bi20 is able to induce killing of CLL B cells in an autologous setting without the addition of effector cells from healthy donors. Therefore, we incubated PBMCs derived from CLL patients with Bi20 and control antibodies. Due to the unfavorable E:T ratio and the known T cell anergy in CLL, cells were incubated for at least 6 days (except for patient CLL 10), and antibodies were added every third day. Analyses of B cell depletion and T cell activation were performed between days 6 and 10, except in the case of patient CLL 10 (day 3).

Figure 11A:
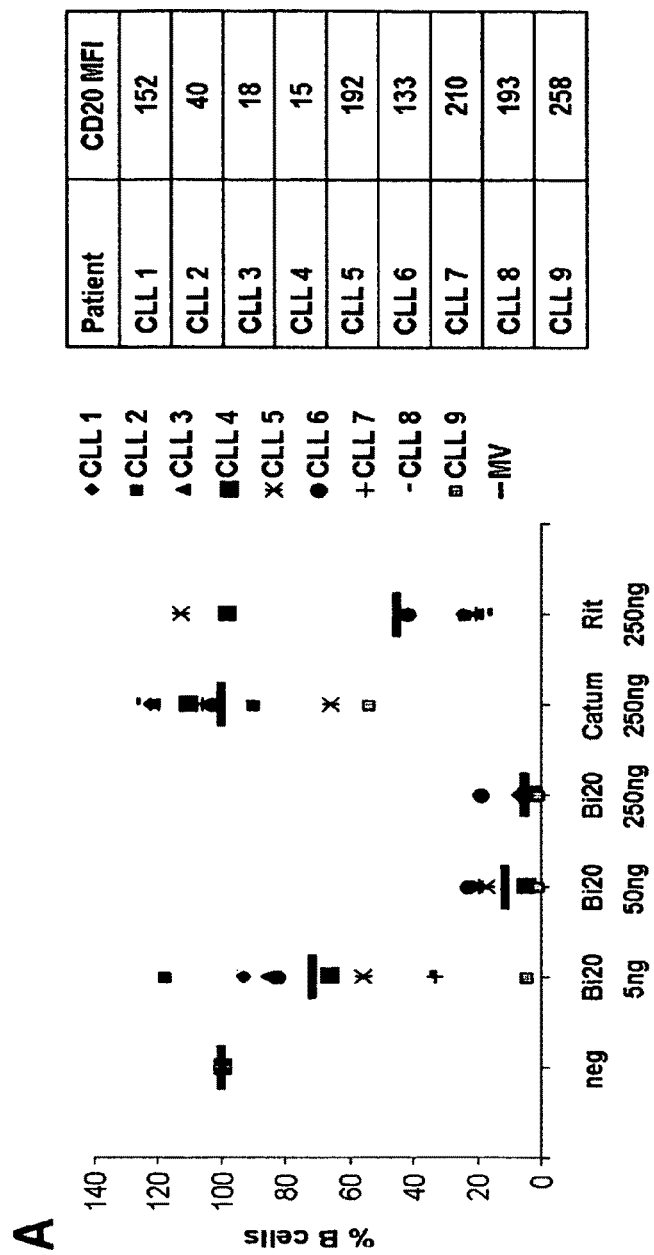
Figure 11B:
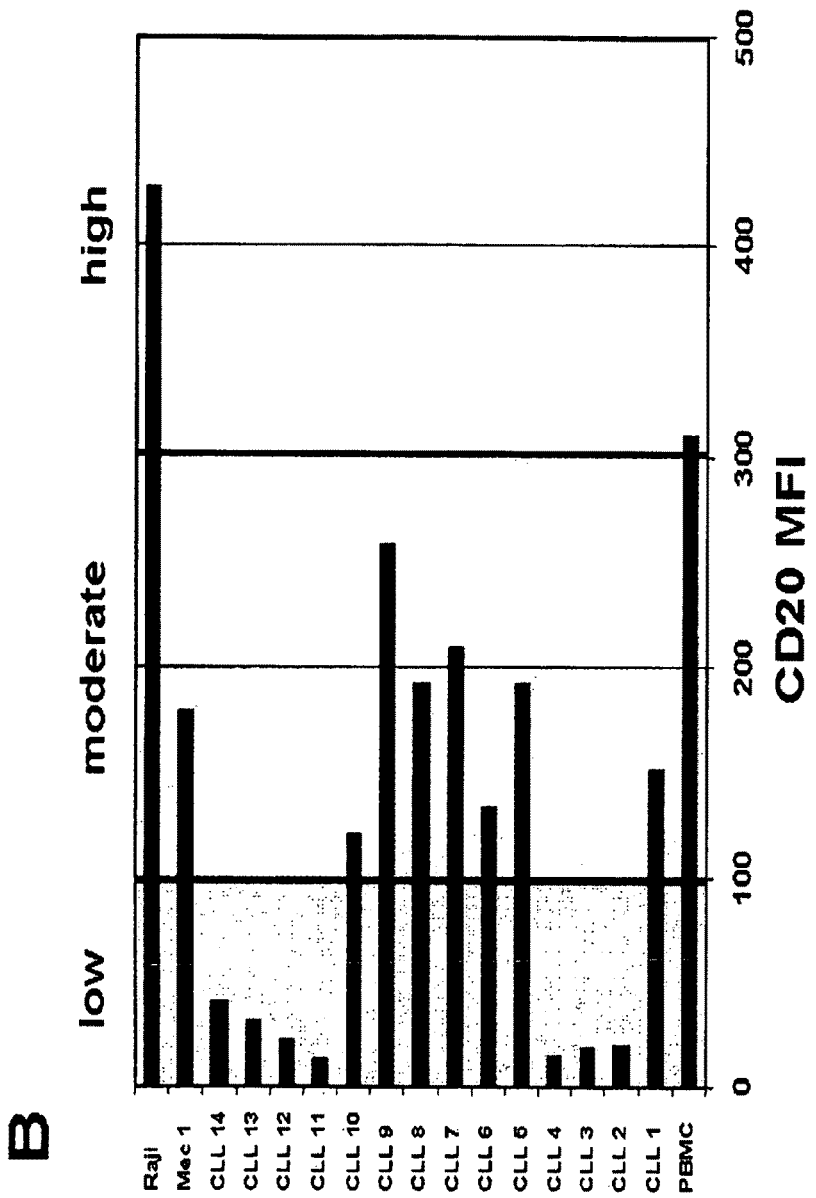

As summarized in Table 2, efficient B cell depletion (>85%) was detected in three of seven patient samples analyzed. In one sample (patient CLL 13), 65% tumor B cell depletion was observed. Interestingly, B cell depletion was observed even at very low CD20 expression levels (patients CLL 11, 12, and 13, FIG. 11B), confirming the results obtained in the allogeneic setting (FIGS. 11A and B). Control experiments with Rituximab, at the same concentrations, showed no or a very low reduction in CLL B cells.

Efficient B cell depletion seems to depend on the effector-to-target ratio (E:T). Patient samples with the best responses (CLL 10, 11, and 12) also had the highest percentages of effector cells. In particular, the sample with the most favorable E:T ratio (3.5:1; derived from patient CLL 10) displayed efficient B cell elimination after only 3 days.

CLL T cells are known to be anergic, notably the CD4 subset.[34] Surprisingly, when we analyzed activation of the $CD4^+$ and $CD8^+$ T cell subsets by CD25 up-regulation at the end of the incubation period, we found that in five of six patient samples efficient activation of both the $CD4^+$ and $CD8^+$ subsets had occurred (Table 2). No activation was seen when samples were treated with Rituximab (data not shown). These results show that, at least in vitro, Bi20 could overcome T cell anergy in CLL samples, even in the presence of tumor cells.

Despite promising results in the treatment of B cell lymphomas using the anti-CD20 monoclonal antibody Rituximab (especially in combination with chemotherapy), patients eventually relapse.[9,35] Therefore, there is a need for further therapeutic options. One improvement might be the use of bispecific antibodies, which redirect effector cells such as T cells to the tumor cells.

Bispecific antibodies directed against B cell-specific antigens such as CD19 or CD20 have been under intensive investigation for the last 10-15 years, but limited clinical data showing only moderate responses[14,36,37] are available thus far. Moreover, the complicated and inefficient manufacturing process makes it difficult to produce sufficient amounts of antibody for clinical use. Here we describe the generation and production of Bi20, a new trifunctional bispecific antibody directed against CD20 and CD3. Particularly, the use of the isotype combination mouse IgG2a and rat IgG2b but also of the other trifunctional bispecific antibodies described herein enables the high-yield production of correctly paired bispecific antibodies due to species-restricted heavy/light chain pairing.[30] These trAbs are characterized by simultaneous binding of tumor cells, T cells, and $Fc\gamma RI/III^+$-accessory cells, thus enhancing tumor cell eradication.[17,18]

Bi20 was shown to be very efficient in B cell elimination in vitro without the need for any costimulation. B cell depletion assays demonstrated that even at an antibody concentration as low as 0.5 ng/ml, nearly 70% of Raji tumor B cells could be eliminated after 24 hours, with complete tumor cell eradication after 3 days. Using B cell lines representative of other NHL entities (Mec1, Granta, or DOHH-2), similar results were obtained, indicating that tumor cell elimination is not restricted to certain subgroups of this malignant disease.

Furthermore, B cells derived from CLL patients also were efficiently killed (FIGS. 11A and B, Table 5), despite the increased apoptosis resistance and low CD20 expression levels that are characteristic of CLL B cells.[27,38,39] Again, no pre- or coactivation of T cells was necessary for efficient CLL B cell elimination, in contrast to other bispecific antibodies that have been described. For example, the bispecific mouse antibody Bis20 (mouse IgG1 CD20×mouse IgG2b CD3) induced nearly 60% B cell depletion at the same E:T ratio used in our experiments but with a 10-fold higher antibody concentration, pre-activated T cells, and a shorter incubation time.[40] In another study using an anti-CD20×anti-CD3 diabody, lysis of tumor cells (Raji) could only be achieved when PBLs were pre-stimulated with IL-2. Even at a diabody concentration of 1000 ng/ml and an E:T ratio of 20:1, only about 35% of cells were lysed.[41] Furthermore, Cochlovius and colleagues showed for an anti-CD3×anti-CD19 diabody that pre-activated PBLs and T-cell costimulation via CD28 are necessary for efficient B cell lysis at antibody concentrations of 1-2.5 µg/ml.[32,42]

Bi20 induced efficient tumor cell killing in four of seven patient samples, even in an autologous setting without addition of healthy donor PBMCs. Remarkably, in contrast to Rituximab, Bi20-mediated B cell depletion is even effective in the presence of very low CD20 expression levels by the CLL tumor cells, which holds true for the autologous as well as the allogeneic setting (Table 5 and FIG. 11). This finding is in accordance with clinical data of CLL studies in which Rituximab shows only limited efficacy as a monotherapy, possibly due to low CD20 expression by the CLL tumor cells.[3,43]

In contrast to several other bispecific antibodies,[44,45] Bi20 efficiently activated both $CD4^+$ and $CD8^+$ T-cell subsets, even in the absence of any costimulatory molecules such as anti-CD28 antibodies or IL-2. Consequently, we detected high levels of INF-γ, which is known to be released by stimulated T cells and which is an indicator of a Th1-type response.[46] T cell activation was also accompanied by proliferation of both T-cell subsets.

T-cell activation was not only observed using healthy donor T cells but also with T cells from B-CLL patients (Table 5). These T cells are often characterized by anergy, probably due to low CD28 and T-cell receptor expression.[47,48] In our experiments, activation of the $CD4^+$ and $CD8^+$ T-cell subsets was detected even in those samples in which no substantial CLL B cell depletion was observed. The limited B cell depletion in some samples (CLL-2, -4, -14) might be due to the short incubation period that is restricted by the limited viability of B-CLL cells in vitro. A comparable B-cell depletion based on coactivator-independent T-cell activation was recently described with a single chain CD19×CD3 bispecific antibody, further confirming the potency of the bispecific antibody format.[49,50] Thus, our results indicate that Bi20 might have the potential to overcome CLL T cell anergy not only in vitro but also in vivo.

In addition to T cells, Bi20 also binds to and activates Fcγ-RI+ cells. Activation is dependent on concomitant binding of Bi20 to T cells because binding of tumor target cells and Fcγ-RI+ cells is not sufficient for activation, as shown with the parental antibody TPA10 (FIGS. 10A and B). The importance of the Fc region of trAbs is supported by our recent observation that in an immunocompetent mouse B cell lymphoma model, the induction of long-lasting antitumor immunity was dependent on a functional Fc part of the trAb. In these experiments, the use of a F(ab)₂ fragment of a trAb significantly diminished survival of these mice.[20] This result is consistent with a recent publication[51] showing that a diabody combination of anti-CD19×anti-FcγRIII and anti-CD19×anti-CD3 showed higher antitumor activity compared to a single diabody in vitro and in a mouse model, although in both cases additional costimulation of T cells via an anti-CD28 antibody was necessary. These results indicate that simultaneous binding and activation of T cells and FcγR+ effector cells as mediated by Bi20 allows more efficient tumor cell killing than binding to tumor cells and T cells alone.

Taken together, our results show that trAb Bi20 is a potent inducer of tumor B cell depletion that is not dependent on any pre- or coactivation, even when CD20 expression by the tumor cells is very low. The simultaneous activation of T cells and accessory immune cells and their redirection to the tumor cells overcomes the T cell anergy described for CLL, not only in vitro but also in vivo. Therefore, the trifunctional bispecific antibodies described herein offer new therapeutic options to treat previously incurable non-Hodgkin's lymphoma and CLL also in patients wherein the expression of CD20 is as low as described in the present description.

REFERENCES

1. Greiner T C, Medeiros L J, Jaffe E S. Non-Hodgkin's lymphoma. Cancer. 1995; 75:370-380.
2. Ries L A G, Harkins D, Krapcho M, et al. SEER Cancer Statistics Review, 1975-2003.
   Bethesda, Md.: National Cancer Institute, 2006.
3. Lin T S, Lucas M S, Byrd J C. Rituximab in B-cell chronic lymphocytic leukemia. Semin Oncol. 2003; 30:483-492.
4. Dillman R O. Treatment of low-grade B-cell lymphoma with the monoclonal antibody rituximab. Semin Oncol. 2003; 30:434-447.
5. Blum K A, Bartlett N L. Antibodies for the treatment of diffuse large cell lymphoma.
   Semin Oncol. 2003; 30:448-456.
6. Moreton P, Hillmen P. Alemtuzumab therapy in B-cell lymphoproliferative disorders.
   Semin Oncol. 2003; 30:493-501.
7. Hiddemann W, Dreyling M, Unterhalt M. Rituximab plus chemotherapy in follicular and mantle cell lymphomas. Semin Oncol. 2003; 30:16-20.
8. Montserrat E. Rituximab in chronic lymphocytic leukemia. Semin Oncol. 2003; 30:34-39.
9. Smith M R. Rituximab (monoclonal anti-CD20 antibody): mechanisms of action and resistance. Oncogene. 2003; 22:7359-7368.
10. Mavromatis B H, Cheson B D. Novel therapies for chronic lymphocytic leukemia.
    Blood Rev. 2004; 18:137-148.
11. Nagy Z A, Hubner B, Lohning C, et al. Fully human, HLA-DR-specific monoclonal antibodies efficiently induce programmed death of malignant lymphoid cells. Nat Med. 2002; 8:801-807.
12. Baeuerle P A, Kufer P, Lutterbuse R. Bispecific antibodies for polyclonal T-cell engagement. Curr Opin Mol Ther. 2003; 5:413-419.
13. Peipp M, Valerius T. Bispecific antibodies targeting cancer cells. Biochem Soc Trans. 2002; 30:507-511.
14. Manzke O, Tesch H, Borchmann P, et al. Locoregional treatment of low-grade B-cell lymphoma with CD3×CD19 bispecific antibodies and CD28 costimulation. I. Clinical phase I evaluation. Int J Cancer. 2001; 91:508-515.
15. Manzke O, Tesch H, Lorenzen J, Diehl V, Bohlen H. Locoregional treatment of low-grade B-cell lymphoma with CD3×CD19 bispecific antibodies and CD28 costimulation. II. Assessment of cellular immune responses. Int J Cancer. 2001; 91:516-522.
16. Haagen I A. Performance of CD3×CD19 bispecific monoclonal antibodies in B cell malignancy. Leuk Lymphoma. 1995; 19:381-393.
17. Zeidler R, Mysliwietz J, Csanady M, et al. The Fc-region of a new class of intact bispecific antibody mediates activation of accessory cells and NK cells and induces direct phagocytosis of tumour cells. Br J Cancer. 2000; 83:261-266.
18. Zeidler R, Reisbach G, Wollenberg B, et al. Simultaneous activation of T cells and accessory cells by a new class of intact bispecific antibody results in efficient tumor cell killing. J Immunol. 1999; 163:1246-1252.
19. Lindhofer H, Menzel H, Gunther W, Hultner L, Thierfelder S. Bispecific antibodies target operationally tumor-specific antigens in two leukemia relapse models. Blood. 1996; 88:4651-4658.
20. Ruf P, Lindhofer H. Induction of a long-lasting antitumor immunity by a trifunctional bispecific antibody. Blood. 2001; 98:2526-2534.
21. Heiss M M, Strohlein M A, Jager M, et al. Immunotherapy of malignant ascites with trifunctional antibodies. Int J Cancer. 2005; 117:435-443.
22. Riesenberg R, Buchner A, Pohla H, Lindhofer H. Lysis of prostate carcinoma cells by trifunctional bispecific antibodies (alpha EpCAM×alpha CD3). J Histochem Cytochem. 2001; 49:911-917.
23. Kiewe P, Hasmuller S, Kahlert S, et al. Phase I trial of the trifunctional anti-HER2×anti-CD3 antibody ertumaxomab in metastatic breast cancer. Clin Cancer Res. 2006; 12:3085-3091.
24. Tedder T F, Engel P. CD20: a regulator of cell-cycle progression of B lymphocytes.
    Immunol Today. 1994; 15:450-454.
25. O'Keefe T L, Williams G T, Davies S L, Neuberger M S. Mice carrying a CD20 gene disruption. Immunogenetics. 1998; 48:125-132.
26. Nadler L M, Ritz J, Hardy R, Pesando J M, Schlossman S F, Stashenko P. A unique cell surface antigen identifying lymphoid malignancies of B cell origin. J Clin Invest. 1981; 67:134-140.
27. Delgado J, Matutes E, Morilla A M, et al. Diagnostic significance of CD20 and FMC7 expression in B-cell disorders. Am J Clin Pathol. 2003; 120:754-759.
28. Anderson K C, Bates M P, Slaughenhoupt B L, Pinkus G S, Schlossman S F, Nadler L M. Expression of human B cell-associated antigens on leukemias and lymphomas: a model of human B cell differentiation. Blood. 1984; 63:1424-1433.
29. Press O W, Howell-Clark J, Anderson S, Bernstein I. Retention of B-cell-specific monoclonal antibodies by human lymphoma cells. Blood. 1994; 83:1390-1397.
30. Lindhofer H, Mocikat R, Steipe B, Thierfelder S. Preferential species-restricted heavy/light chain pairing in rat/mouse quadromas. Implications for a single-step purification of bispecific antibodies. J Immunol. 1995; 155:219-225.

31. Ruf P, Jager M, Ellwart J, Wosch S, Kusterer E, Lindhofer H. Two new trifunctional antibodies for the therapy of human malignant melanoma. Int J Cancer. 2004; 108:725-732.
32. Cochlovius B, Kipriyanov S M, Stassar M J, et al. Treatment of human B cell lymphoma xenografts with a CD3×CD19 diabody and T cells. J Immunol. 2000; 165:888-895.
33. Winkler U, Jensen M, Manzke O, Schulz H, Diehl V, Engert A. Cytokine-release syndrome in patients with B-cell chronic lymphocytic leukemia and high lymphocyte counts after treatment with an anti-CD20 monoclonal antibody (rituximab, IDEC-C2B8). Blood. 1999; 94:2217-2224.
34. Bartik M M, Welker D, Kay N E. Impairments in immune cell function in B cell chronic lymphocytic leukemia. Semin Oncol. 1998; 25:27-33.
35. Ghielmini M. Multimodality therapies and optimal schedule of antibodies: rituximab in lymphoma as an example. Hematology (Am Soc Hematol Educ Program). 2005:321-328.
36. Weiner G J, De Gast G C. Bispecific monoclonal antibody therapy of B-cell malignancy. Leuk Lymphoma. 1995; 16:199-207.
37. De Gast G C, Van Houten A A, Haagen I A, et al. Clinical experience with CD3×CD19 bispecific antibodies in patients with B cell malignancies. J Hematother. 1995; 4:433-437.
38. Huh Y O, Keating M J, Saffer H L, Jilani I, Lerner S, Albitar M. Higher levels of surface CD20 expression on circulating lymphocytes compared with bone marrow and lymph nodes in B-cell chronic lymphocytic leukemia. Am J Clin Pathol. 2001; 116:437-443.
39. Reed J C, Kitada S, Kim Y, Byrd J. Modulating apoptosis pathways in low-grade B-cell malignancies using biological response modifiers. Semin Oncol. 2002; 29:10-24.
40. Withoff S, Bijman M N, Stel A J, et al. Characterization of BIS20×3, a bi-specific antibody activating and retargeting T-cells to CD20-positive B-cells. Br J Cancer. 2001; 84:1115-1121.
41. Xiong D, Xu Y, Liu H, et al. Efficient inhibition of human B-cell lymphoma xenografts with an anti-CD20×anti-CD3 bispecific diabody. Cancer Lett. 2002; 177:29-39.
42. Kipriyanov S M, Moldenhauer G, Strauss G, Little M. Bispecific CD3×CD19 diabody for T cell-mediated lysis of malignant human B cells. Int J Cancer. 1998; 77:763-772.
43. Nguyen D T, Amess J A, Doughty H, Hendry L, Diamond L W. IDEC-C2B8 anti-CD20 (rituximab) immunotherapy in patients with low-grade non-Hodgkin's lymphoma and lymphoproliferative disorders: evaluation of response on 48 patients. Eur J Haematol. 1999; 62:76-82.
44. Manzke O, Berthold F, Huebel K, Tesch H, Diehl V, Bohlen H. CD3×CD19 bispecific antibodies and CD28 bivalent antibodies enhance T-cell reactivity against autologous leukemic cells in pediatric B-ALL bone marrow. Int J Cancer. 1999; 80:715-722.
45. Manzke O, Titzer S, Tesch H, Diehl V, Bohlen H. CD3×CD19 bispecific antibodies and CD28 costimulation for locoregional treatment of low-malignancy non-Hodgkin's lymphoma. Cancer Immunol Immunother. 1997; 45:198-202.
46. Berenson L S, Ota N, Murphy K M. Issues in T-helper 1 development—resolved and unresolved. Immunol Rev. 2004; 202:157-174.
47. Mellstedt H, Choudhury A. T and B cells in B-chronic lymphocytic leukaemia: Faust, Mephistopheles and the pact with the Devil. Cancer Immunol Immunother. 2006; 55:210-220.
48. Rossi E, Matutes E, Morilla R, Owusu-Ankomah K, Heffernan A M, Catovsky D. Zeta chain and CD28 are poorly expressed on T lymphocytes from chronic lymphocytic leukemia.
Leukemia. 1996; 10:494-497.
49. Dreier T, Lorenczewski G, Brandl C, et al. Extremely potent, rapid and costimulation-independent cytotoxic T-cell response against lymphoma cells catalyzed by a single-chain bispecific antibody. Int J Cancer. 2002; 100: 690-697.
50. Loffler A, Gruen M, Wuchter C, et al. Efficient elimination of chronic lymphocytic leukaemia B cells by autologous T cells with a bispecific anti-CD19/anti-CD3 single-chain antibody construct. Leukemia. 2003; 17:900-909.
51. Kipriyanov S M, Cochlovius B, Schafer H J, et al. Synergistic antitumor effect of bispecific CD19×CD3 and CD19×CD16 diabodies in a preclinical model of non-Hodgkin's lymphoma. J Immunol. 2002; 169:137-144.
52. Slamon D J, Clark G M, Wong S G, Levin W J, Ullrich A, McGuire W L. Human breast cancer: correlation of relapse and survival with amplification of the HER-2/neu oncogene. Science 1987; 235(4785):177-82.
53. Slamon D J, Godolphin W, Jones L A, Holt J A, Wong S G, Keith D E et al. Studies of the HER-2/neu proto-oncogene in human breast and ovarian cancer. Science 1989; 244 (4905):707-12.
54. Hynes N E, Stern D F. The biology of erbB-2/neu/HER-2 and its role in cancer. Biochim. Biophys. Acta 1994; 1198 (2-3):165-84.
55. Lewis G D, Figari I, Fendly B, Wong W L, Carter P, Gorman C et al. Differential responses of human tumor cell lines to anti-p185HER2 monoclonal antibodies. Cancer Immunol. Immunother. 1993; 37(4):255-63.
56. Sarup J C, Johnson R M, King K L, Fendly B M, Lipari M T, Napier M A et al. Characterization of an anti-p185HER2 monoclonal antibody that stimulates receptor function and inhibits tumor cell growth. Growth Regul. 1991; 1(2):72-82.
57. Paik S, Bryant J, Tan-Chiu E, Romond E, Hiller W, Park K et al. Real-world performance of HER2 testing—ational Surgical Adjuvant Breast and Bowel Project experience. J. Natl. Cancer Inst. 2002; 94(11):852-4.
58. Hudziak R M, Lewis G D, Winget M, Fendly B M, Shepard H M, Ullrich A. p185HER2 monoclonal antibody has antiproliferative effects in vitro and sensitizes human breast tumor cells to tumor necrosis factor. Mol. Cell Biol. 1989; 9(3):1165-72.
59. Zeidler R, Mayer A, Gires O, Schmitt B, Mack B, Lindhofer H et al. TNFalpha contributes to the antitumor activity of a bispecific, trifunctional antibody. Anticancer Res. 2001; 21(5):3499-503.

TABLE 1

Characteristics of used antibodies and their corresponding detection antibodies

| Antibody name | Antibody type | Specifity for | Isotype | Detection antibody (FITC) |
|---|---|---|---|---|
| REXOMUN ® * | trifunctional | Her2/neu × CD3 | mouse IgG2a × rat IgG2b | anti rat IgG H + L FITC |
| Trastuzumab $ | monoclonal | Her2/neu | human IgG1 | anti human IgG1 FITC |

TABLE 1-continued

Characteristics of used antibodies and their corresponding detection antibodies

| Antibody name | Antibody type | Specifity for | Isotype | Detection antibody (FITC) |
|---|---|---|---|---|
| 520C9 | monoclonal | Her2/neu | mouse IgG1 | anti mouse IgG1 FITC |
| EGFR-I | monoclonal | EGFRI | mouse IgG2a | ALEXA FLUOR ® 477 anti mouse IgG2a |
| A45-B-B3 # | monoclonal | CK 8, 18, 19 | mouse IgG1 | ALEXA FLUOR ® 477 anti mouse IgG1 |

\* TRION Pharma, Munich;
$ Roche;
Micromet, Munich

TABLE 2

Used cell lines and their Her2/neu score

| Cell line | Origin | Number of molecules on cell surface* | Her2/neu score | Method |
|---|---|---|---|---|
| SKBR3 | Breast | 1.000.000-20.000.000 | +3 | HERCEPTEST ®, FACS |
| HCT-8 | Colon | 80.000-110.000 | +1 | HERCEPTEST ®, FACS |
| Lox | Melanoma | <20.000 | negative | FACS, Cytospin |

*according to Ross et al., Molecular and Cellular Proteomics 3: 379-398, 2004

TABLE 3

Clonogenic assay samples

| | PBMC + SKBR3 (Her2 +3) | | | PBMC + HCT-8 (Her2 +1) | | | PBMC + Lox (Her2 0) | | | Control samples | |
|---|---|---|---|---|---|---|---|---|---|---|---|
| | Trastuzumab | REXOMUN ® | | Trastuzumab | REXOMUN ® | | Trastuzumab | REXOMUN ® | | Cells | Ab |
| A4 | 100 µg/ml | — | B4 | 100 µg/ml | — | C4 | 100 µg/ml | — | A2, B2, C2 | PBMC | — |
| A5 | 50 µg/ml | — | B5 | 50 µg/ml | — | C5 | 50 µg/ml | — | A1 | SKBR3 | — |
| A6 | 20 µg/ml | — | B6 | 20 µg/ml | — | C6 | 20 µg/ml | — | B1 | HCT-8 | — |
| A7 | 10 µg/ml | — | B7 | 10 µg/ml | — | C7 | 10 µg/ml | — | C1 | Lox | — |
| A8 | 1 µg/ml | — | B8 | 1 µg/ml | — | C8 | 1 µg/ml | — | A3 | PBMC + SKBR3 | — |
| A9 | | 100 ng/ml | B9 | | 100 ng/ml | C9 | | 100 ng/ml | B3 | PBMC + HCT-8 | — |
| A10 | — | 50 ng/ml | B10 | — | 50 ng/ml | C10 | — | 50 ng/ml | C3 | PBMC + Lox | — |
| A11 | — | 10 ng/ml | B11 | — | 10 ng/ml | C11 | — | 10 ng/ml | | | |
| A12 | — | 1 ng/ml | B12 | — | 1 ng/ml | C12 | — | 1 ng/ml | | | |

Ab = Antibody,
µg = micrograms,
ng = nanograms

TABLE 4

Bi20 mediates cytokine secretion

| | | INFγ | IL-6 | TNFα | IL-10 | IL-4 | IL-2 |
|---|---|---|---|---|---|---|---|
| Raji | Neg | 8947 | 821 | 420 | 81 | 16 | 1299 |
| | Bi20 | 143631 | 7503 | 1261 | 2012 | 101 | 11559 |
| | Catum | 157624 | 3505 | 741 | 433 | 16 | 10 |
| | Rituximab | 24148 | 3702 | 411 | 90 | 13 | 748 |
| | 26II6/TPA10 | 61910 | 5050 | 112 | 555 | 10 | 8 |
| Mec1 | Neg | 13086 | 1109 | 486 | 641 | 20 | 1257 |
| | Bi20 | 49905 | 5773 | 1347 | 3101 | 70 | 3457 |
| | Catum | 131770 | 2962 | 1758 | 1222 | 12 | 10 |
| | Rituximab | 32225 | 3666 | 205 | 268 | 17 | 700 |
| | 26II6/TPA10 | 43951 | 2393 | 428 | 652 | 19 | 8 |
| Ramos | Neg | 6336 | 214 | 264 | 114 | 46 | 112 |
| | Bi20 | 67806 | 4524 | 1033 | 3298 | 22 | 1256 |
| | Catum | 97615 | 2408 | 762 | 1156 | 53 | 10 |
| | Rituximab | 13413 | 1570 | 188 | 148 | 24 | 73 |
| DOHH-2 | Neg | 68 | 117 | 14 | 30 | 5 | 17 |
| | Bi20 | 110309 | 4314 | 402 | 1543 | 22 | 13 |
| | Catum | 116321 | 2980 | 168 | 578 | 6 | 20 |
| | Rituximab | 242 | 440 | 16 | 24 | 10 | 22 |
| Granta | Neg | 8393 | 355 | 391 | 157 | 16 | 228 |
| | Bi20 | 92807 | 6968 | 2479 | 1652 | 39 | 3939 |
| | Catum | 184439 | 3364 | 1518 | 444 | 19 | 6 |
| | Rituximab | 16259 | 3496 | 154 | 105 | 12 | 74 |

TABLE 5

Bi20 mediates elimination of CLL B cells in vitro in an autologous setting

| patient | B cells (%) | T cells (%) | CD20 MFI | E:T | [Ab] ng/ml | day | B-cell depletion (%) Bi20 | Rit | T-cell activation |
|---|---|---|---|---|---|---|---|---|---|
| CLL 2 | 89.3 | 4.6 | 40 | 1:16 | 250 | 6 | 18 | 16 | ++ |
| CLL 4 | 90 | 3.4 | 15 | 1:22 | 500 | 6 | 3 | 7 | ++ |
| CLL 10 | 22.2 | 54.1 | 120 | 3.5:1 | 200 | 3 | 88 | n.d | ++ |
| CLL 11 | 62 | 21.9 | 13 | 1:2.1 | 500 | 6 | 89 | 36 | ++ |
| CLL 12 | 56 | 24.2 | 22 | 1:1.7 | 500 | 9 | 100 | 0 | n.d |
| CLL 13 | 86 | 15.6 | 31 | 1:4.3 | 500 | 10 | 65 | 10 | − |
| CLL 14 | 76.8 | 10.9 | 41 | 1:5.2 | 250 | 6 | 0 | 0 | ++ |

The invention claimed is:

1. A method for the treatment of tumor diseases in a patient, comprising:
    (a) providing a patient with a tumor cell expressing a tumor-associated antigen selected from the group consisting of Her2/neu, CD20, EpCam, GD2, and GD3, wherein the tumor-associated antigen is expressed on said tumor cell:
        (i) in an amount of about 5,000-150,000 tumor-associated antigens/tumor cell for Her2/neu; or
        (ii) in an amount of about up to 500,000 tumor-associated antigens/tumor cell for Her2/neu in tumor cells tested FISH negative; or
        (iii) in an amount of about 1,000 to about 350,000 tumor-associated antigens/tumor cell for CD20; or
        (iv) in an amount of about 1,000 to about 350,000 tumor-associated antigens/tumor cell for EpCAM, GD2, and GD3; and
    (b) administering to said patient a pharmaceutically effective amount of a trifunctional bispecific antibody having the following properties:
        1. a first binding arm that binds to a T cell;
        2. a second binding arm that binds to said tumor-associated antigen expressed on said tumor cell; and
        3. an Fc-portion that binds to Fcγ-receptor type I or III positive cells, or a combination thereof.

2. The method according to claim 1, wherein said tumor-associated antigen is Her2/neu or CD20.

3. The method according to claim 1 or 2, wherein said tumor-associated antigen is expressed on the tumor cells in amount of at least about 5,000, 20,000, 50,000 or 80,000 tumor-associated antigens/tumor cell and at a maximum of about 150,000, 110,000 or 100,000 tumor-associated antigens/tumor cell.

4. The method according to claim 1, wherein said trifunctional antibody is selected from the group consisting of an anti-CD3×anti-tumor-associated antigen antibody, anti-CD4×anti-tumor-associated antigen antibody, anti-CD5× anti-tumor-associated antigen antibody, anti-CD6×anti-tumor-associated antigen antibody, anti-CD8 anti-tumor-associated antigen antibody, anti-CD2×anti-tumor-associated antigen antibody, anti-CD28×anti-tumor-associated antigen antibody, anti-CD44×anti-tumor-associated antigen antibody or a combination thereof.

5. The method according to claim 1, wherein said trifunctional antibody is a heterologous bispecific antibody.

6. The method according to claim 5, wherein said antibody is a heterologous rat/mouse bispecific antibody.

7. The method according to claim 1, wherein said trifunctional antibody is selected from at least one member of the following group of isotype combinations in its Fc-region: rat-IgG2b/mouse-IgG2a, rat-IgG2b/mouse-IgG2b, rat-IgG2b/human-IgG, rat-IgG2b/human-IgG2.

8. The method according to claim 1, wherein said trifunctional antibody is administered in an amount of 0.05-15 µg/kg body weight.

9. The method according to claim 1, wherein said trifunctional bispecific antibody is an anti-Her2/neu×anti-CD3 antibody binding to Fcγ-type I/III-receptors.

10. The method according to claim 9, wherein said antibody has the isotype combination rat-IgG2b/mouse-IgG2a.

11. The method according to claim 1, wherein said Her2/neu antigen is expressed in an amount of about 5,000-150,000.

12. The method according to claim 11, wherein said Her2/neu antigen is expressed in an amount of about 20,000-100,000 on breast tumor cells.

13. The method according to claim 1, wherein said Her2/neu antigen is expressed in an amount of up to 500,000 and the tumor cells are FISH negative.

14. The method according to claim 13, wherein the cancer is a breast cancer.

15. The method according to claim 1, wherein said trifunctional bispecific antibody is an anti-CD20×anti-CD3 antibody binding to Fcγ-type I/III-receptor.

16. The method according to claim 15, wherein said antibody has the isotype combination rat-IgG2b/mouse-IgG2a.

17. The method according to claim 1, wherein said tumor-associated antigen is CD20 and is expressed on said tumor cell in an amount of up to 300,000 tumor-associated antigens/tumor cell.

18. The methods according to claim 1, wherein said tumor-associated antigen is EpCAM, GD2, or GD3, and is expressed on said tumor cell in an amount of about 1,000 to about 300,000 tumor-associated antigens/tumor cell.

* * * * *